United States Patent [19]
Hamm et al.

[11] Patent Number: 5,546,948
[45] Date of Patent: * Aug. 20, 1996

[54] ULTRASOUND IMAGING GUIDEWIRE

[75] Inventors: Mark A. Hamm, Malden; Robert J. Crowley, Wayland, Mass.

[73] Assignee: Boston Scientific Corporation, Watertown, Mass.

[ * ] Notice: The term of this patent shall not extend beyond the expiration date of Pat. No. 5,368,035.

[21] Appl. No.: 345,616

[22] Filed: Nov. 28, 1994

Related U.S. Application Data

[63] Continuation of Ser. No. 946,809, Sep. 17, 1992, Pat. No. 5,368,035, which is a continuation of Ser. No. 839,178, Feb. 21, 1992, abandoned, which is a continuation-in-part of Ser. No. 570,319, Aug. 21, 1990, abandoned.

[51] Int. Cl.$^6$ ........................................ A61B 8/12
[52] U.S. Cl. ................................. 128/662.060; 128/772
[58] Field of Search .................... 128/660.030, 662.060, 128/772; 606/159, 194

[56] References Cited

U.S. PATENT DOCUMENTS

| | | | |
|---|---|---|---|
| 1,167,014 | 1/1916 | O'Brien | 606/151 |
| 2,029,495 | 2/1936 | Lowe | 128/305 |
| 2,545,101 | 3/1951 | Meunier | 171/327 |
| 2,779,334 | 1/1957 | Sandborn | 128/303 |
| 2,949,910 | 8/1960 | Brown et al. | 128/2.05 |
| 3,256,733 | 6/1966 | Carlin | 73/67.8 |
| 3,542,014 | 11/1970 | Peroneau | 128/2 |
| 3,547,101 | 12/1970 | Rosauer | 128/2 |
| 3,614,953 | 10/1971 | Moss | 128/305 |
| 3,704,711 | 12/1972 | Park | 128/305 |
| 3,747,085 | 7/1973 | Willson et al. | 128/2 B |
| 3,749,086 | 7/1973 | Kline et al. | 128/2 M |
| 3,762,416 | 10/1973 | Moss et al. | 128/305 |
| 3,773,034 | 10/1973 | Burns et al. | 128/2 M |
| 3,779,234 | 12/1973 | Eggleton et al. | 128/2 V |

(List continued on next page.)

FOREIGN PATENT DOCUMENTS

| | | |
|---|---|---|
| 0163502 | 4/1985 | European Pat. Off. . |
| 0139574 | 5/1985 | European Pat. Off. . |
| 0214063A1 | 3/1987 | European Pat. Off. . |
| 0397054A2 | 11/1990 | European Pat. Off. . |
| 0423895A1 | 4/1991 | European Pat. Off. . |

(List continued on next page.)

OTHER PUBLICATIONS

Segal et al., "A Doppler Guidewire Used to Assess Coronary Flow During PTCA in Humans" (from Supplement to Circulation, Abstracts from 63rd Scientific Sesssions, Am. Heart Assoc.; vol. 82, No. 4, Oct. 1990 pp. III–662.

(List continued on next page.)

*Primary Examiner*—Francis Jaworski
*Attorney, Agent, or Firm*—Fish & Richardson P.C.

[57] ABSTRACT

A medical guidewire has a substantially uniform small diameter throughout its length and incorporates means for lateral acoustic scanning, and the guidewire comprises a proximal connector, an extended main guidewire body portion, an axially elongated transition section, and a floppy tip portion, the main body portion comprises a stationary outer wall including means capable of transmitting torque and, within the outer wall, an elongated rotatable shaft with a distally positioned acoustic imaging transducer mounted thereon, the proximal connector is constructed to be attached to and detached from a drive device to enable a therapeutic device to be introduced over the guidewire, the connector has a stationary portion secured to the outer wall and an inner drive portion secured to the shaft, the floppy tip portion comprises an outer wire coil and a core rod which tapers from a relatively large diameter at a proximal joint with the outer wire coil to a floppy distal tip, and the elongated transition section serves to join the main body portion to the floppy tip section in a manner retaining substantially the same lateral stiffness as the main body portion and sufficient torquability to enable torquing of the floppy tip by torque applied to the proximal end of the guidewire.

20 Claims, 16 Drawing Sheets

U.S. PATENT DOCUMENTS

| | | | |
|---|---|---|---|
| 3,789,841 | 2/1974 | Antoshkiw | 128/2.05 |
| 3,817,089 | 6/1974 | Eggleton et al. | 73/67.8 S |
| 3,837,345 | 9/1974 | Matar | 128/305 |
| 3,938,502 | 2/1976 | Bom | 128/2 V |
| 3,942,530 | 3/1976 | Northeved | 128/303.15 |
| 4,011,869 | 3/1977 | Seiler, Jr. | 128/276 |
| 4,020,829 | 5/1977 | Willson et al. | 128/2 M |
| 4,020,847 | 5/1977 | Clark, III | 128/305 |
| 4,137,920 | 2/1979 | Bonnet | 128/311 |
| 4,176,662 | 12/1979 | Frazer | 128/6 |
| 4,273,128 | 6/1981 | Lary | 128/305 |
| 4,275,597 | 6/1981 | Quedens et al. | 73/618 |
| 4,290,427 | 9/1981 | Chin | 128/304 |
| 4,319,580 | 3/1982 | Colley et al. | 128/661 |
| 4,327,738 | 5/1982 | Green et al. | 128/660 |
| 4,354,500 | 10/1982 | Colley et al. | 128/663 |
| 4,354,501 | 10/1982 | Colley et al. | 128/663 |
| 4,374,525 | 2/1983 | Baba | 128/660 |
| 4,375,818 | 3/1983 | Suwaki et al. | 128/660 |
| 4,391,282 | 7/1983 | Andou et al. | 128/660 |
| 4,431,006 | 2/1984 | Trimmer et al. | 128/660 |
| 4,462,408 | 7/1984 | Silverstein et al. | 128/660 |
| 4,466,443 | 8/1984 | Utsugi | 128/660 |
| 4,475,553 | 10/1984 | Yamaguchi et al. | 128/660 |
| 4,494,549 | 1/1985 | Namba et al. | 128/660 |
| 4,516,972 | 5/1985 | Samson | 604/282 |
| 4,535,759 | 8/1985 | Polk et al. | 128/24 A |
| 4,558,706 | 12/1985 | Nakada et al. | 128/660 |
| 4,572,201 | 2/1986 | Kondo et al. | 128/660 |
| 4,576,177 | 3/1986 | Webster, Jr. | 128/660 |
| 4,605,009 | 8/1986 | Pourcelot et al. | 128/660 |
| 4,674,515 | 6/1987 | Andou et al. | 128/660 |
| 4,715,378 | 12/1987 | Pope Jr., et al. | 128/344 |
| 4,729,384 | 3/1988 | Bazenet | 128/691 |
| 4,732,156 | 3/1988 | Nakamura | 128/660 |
| 4,794,931 | 1/1989 | Yock | 128/660.03 |
| 4,802,487 | 2/1989 | Martin et al. | 128/662.6 |
| 4,830,023 | 5/1989 | de Toledo et al. | 128/772 |
| 4,906,241 | 3/1990 | Noddin et al. | 606/194 |
| 4,932,419 | 6/1990 | de Toledo | 128/772 |
| 4,934,380 | 6/1990 | de Toledo | 128/772 |
| 4,951,677 | 8/1990 | Crowley et al. | 128/662.06 |
| 5,000,185 | 3/1991 | Yock | 128/662.03 |
| 5,024,234 | 6/1991 | Leary et al. | 128/663.01 |
| 5,040,548 | 8/1991 | Yock | 128/898 |
| 5,049,130 | 9/1991 | Powell | 604/96 |
| 5,054,492 | 10/1991 | Scribner et al. | 128/662.060 |
| 5,095,911 | 3/1992 | Pomeranz | 128/662.060 |
| 5,105,818 | 4/1992 | Christian et al. | 128/662.06 |
| 5,201,316 | 4/1993 | Pomeranz | 128/662.06 |
| 5,240,437 | 8/1993 | Christian | 439/668 |
| 5,243,988 | 9/1993 | Sieber et al. | 128/662.060 |
| 5,368,035 | 11/1994 | Hamm et al. | 128/662.060 |
| 5,372,138 | 12/1994 | Crowley | 128/662.06 |

FOREIGN PATENT DOCUMENTS

| | | |
|---|---|---|
| 0464714A1 | 1/1992 | European Pat. Off. . |
| 0466424A1 | 1/1992 | European Pat. Off. . |
| 2424733 | 5/1978 | France . |
| 3619195 | 2/1987 | Germany . |
| 2044103A | 10/1980 | United Kingdom . |
| 2157828A | 10/1985 | United Kingdom . |
| WO83/01893 | 6/1983 | WIPO . |
| WO83/04174 | 12/1983 | WIPO . |
| WO91/14401 | 10/1991 | WIPO . |
| WO91/14394 | 10/1991 | WIPO . |
| WO91/17710 | 11/1991 | WIPO . |
| WO91/17711 | 11/1991 | WIPO . |

OTHER PUBLICATIONS

Crowley et al., "Optimized Ultrasound . . . Systems" (from Intravascular Ultrasound: Techniques, Developments, Clinical Perspectives; Rotterdam Postgraduate School of Card., Kluwer Acad. Publs., Jun. 1989, pp. 145–151.

Bom et al., "Early . . . Ultrasound Devices" (Intravascular Ultrasound: Techniques, Developments, Clinical Perspectives; Rotterdam Postgraduate School of Card., Kluwer Academic Publs., Jun. 1989, pp. 79–88.

Omoto, "Intracardiac Scanning of the Heart . . . Probe" (the Departments of Surgery and Thoracic Surgery, Faculty of Medicine, University of Tokyo, Tokyo, received for publication on Apr. 11, 1967).

Aloka Endo Scan Model 550–520 (date unknown).

Bruel & Kjaar, "Diagnostic Ultrasound" (date unknown).

Cole, "The Pulsed Doppler Coronary Artery Catheter", Circulation vol. 56, No. 1, Jul. 1977.

Hartley et al., "Pulsed Doppler Coronary Artery Catheter Transducers", Cardiovascular Ultrasonic Flowmetry pp. 279–298 Altobelli, ed. Elsevier Science and Publishing Co., 1985.

Kutz et al., "New Vein Stripper and Technique of Stripping," Surgery 29:271–275 (Feb. 1951).

Olympus GF–UM2/EU–M2 (date unknown).

S. S. White Industrial Products brochure (date unknown).

Samuels et al., "In situ Saphenous Vein Arterial Bypass: A Study of the Anatomy Pertinent to Its Use In situ as a Bypass Graft with a Description of a New Venous Valvulotome", Amer. Surgeon 34:122–130 (Feb. 1968).

Skagseth et al., "In situ Vein Bypass: Experiences with New Vein Valve Strippers", Scand. J. Thor. Cardiovasc. Surg. 7:53–58 (1973).

Diethrich et al., "Hydrophilic Guide Wire for Laser–Assisted Angioplasty", Journal of Vascular Surgery, Aug., 1988, vol. 8, No. 2, pp. 201–202.

Cook Incorporated, Wire Guides, 1986.

Gavant, "Improved Guidewire Immobilization Technique for Interventional procedures", AJR 149:629–630, Sep., 1987.

Ginsburg et al., "Hydrophilic Guide Wire for Laser–Assisted Angioplasty", Journal of Vascular Surgery, Mar., 1989, vol. 9, No. 3, pp. 507–508.

Pinto et al., "Thrombogenicity of Teflon Versus Copolymer–Coated Guidewires: Evaluation with Scanning Electron Microscopy", Jun. 21, 1988, pp. 407–410.

Kikuchi et al., "A New Guidewire with Kink–Resistant Core and Low–Friction Coating", CardioVascular and Interventional Radiology, 1989, 12:107–109.

Robinson et al., "A New Torque Guide Wire", Radiology, Nov. 1987, vol. 165, No. 2, pp. 572–573.

Takayasu et al., "Plastic–coated Guide Wire for Hepatic Arteriography", Radiology, Feb. 1988, vol. 166, No. 2, pp. 545–546.

Medi–tech®, Boston Scientific Corporation, "The Glidewire™", Sep., 1991.

Medi–tech®, Boston Scientific Corporation, "The Glidewire™, Introducing the Newest Glidewire Technology", 1992.

Microvasive®, Boston Scientific Corporation, "The Glidewire™, Superelastic Alloy Core Guidewires", 1992.

Medi–tech®, Boston Scientific Corporation, "AmplatzSuper Stiff ™ Guidewires" (no date given).

Medi–tech®, Boston Scientific Corporation, "Platinum Plus™ Guidewire", 1991.

Microevasive®, Boston Scientific Corporation, "Geenen Endotorque ™ Guidewires, Non–kinking, highly torqueable wires", (no date given).

Microevasive™, Boston Scientific Corporation, "The Glidewire™ : The Unique First–Use Guidewire ", 2/1992.

Barnhart et al., "New Guide Wire for High–Flow Infusion", Radiology–SCVIR, Mar. 1990, vol. 174, No. 3, pp. 1058–1059.

Butto et al., "New Heavy–Duty Exchange Guide Wire", Radiology 163:276–278, 1987.

Crowley et al., "Ultrasound Guided Therapeutic Catheters: Recent Developments and Clinical Results" (from Intravascular Ultrasound 1991; Rotterdam Postgraduate School of Cardiology, Kluwer Academic Publishers, Jun. 1991, pp. 145–156).

"Intravascular Ultrasound 1991, Rotterdam Postgraduate School of Cardiology", Kluwer Academic Publishers, Jun. 1991 (a book containing the article listed as ite AQ).

"Intraluminal Ultrasound, A Physician's Guide" (a book published by Strategic Business Development, Inc., 1990, section 4, pp. 81–99).

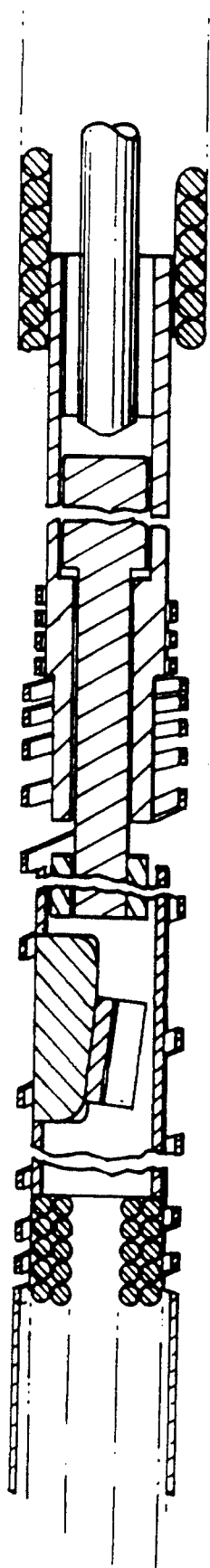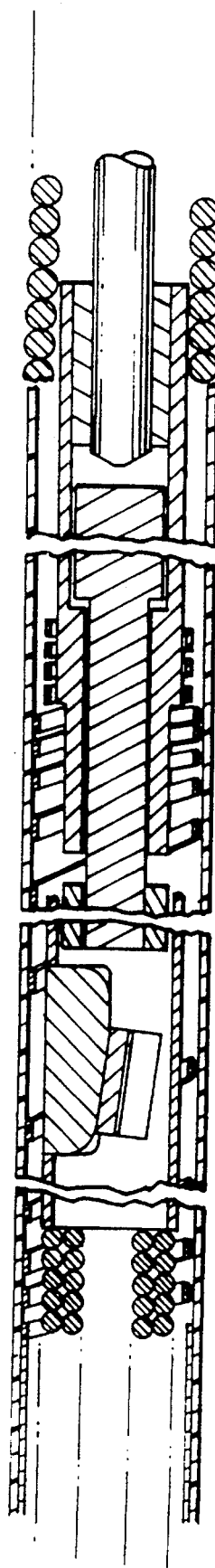
FIG. 2o
FIG. 2p

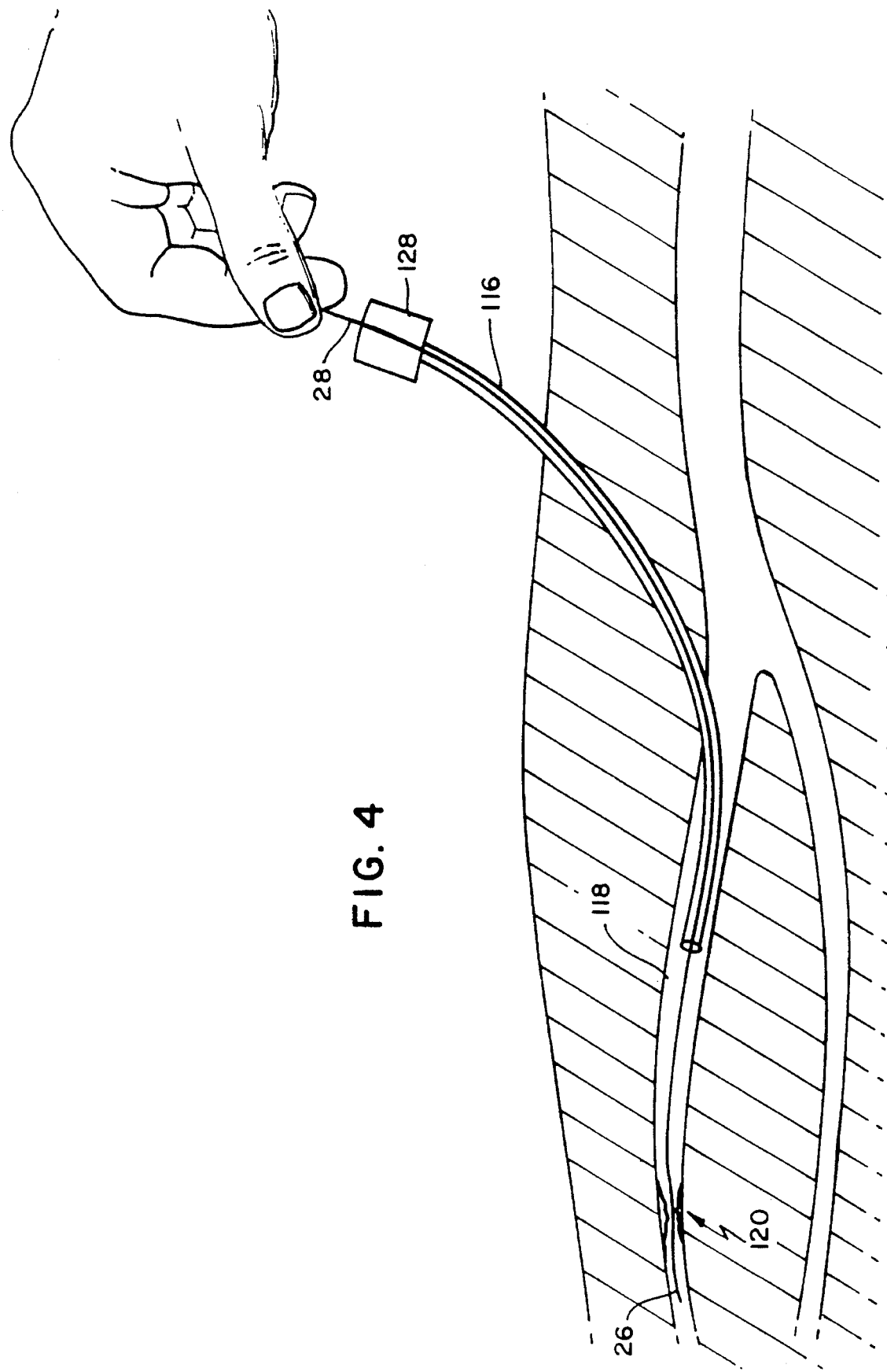

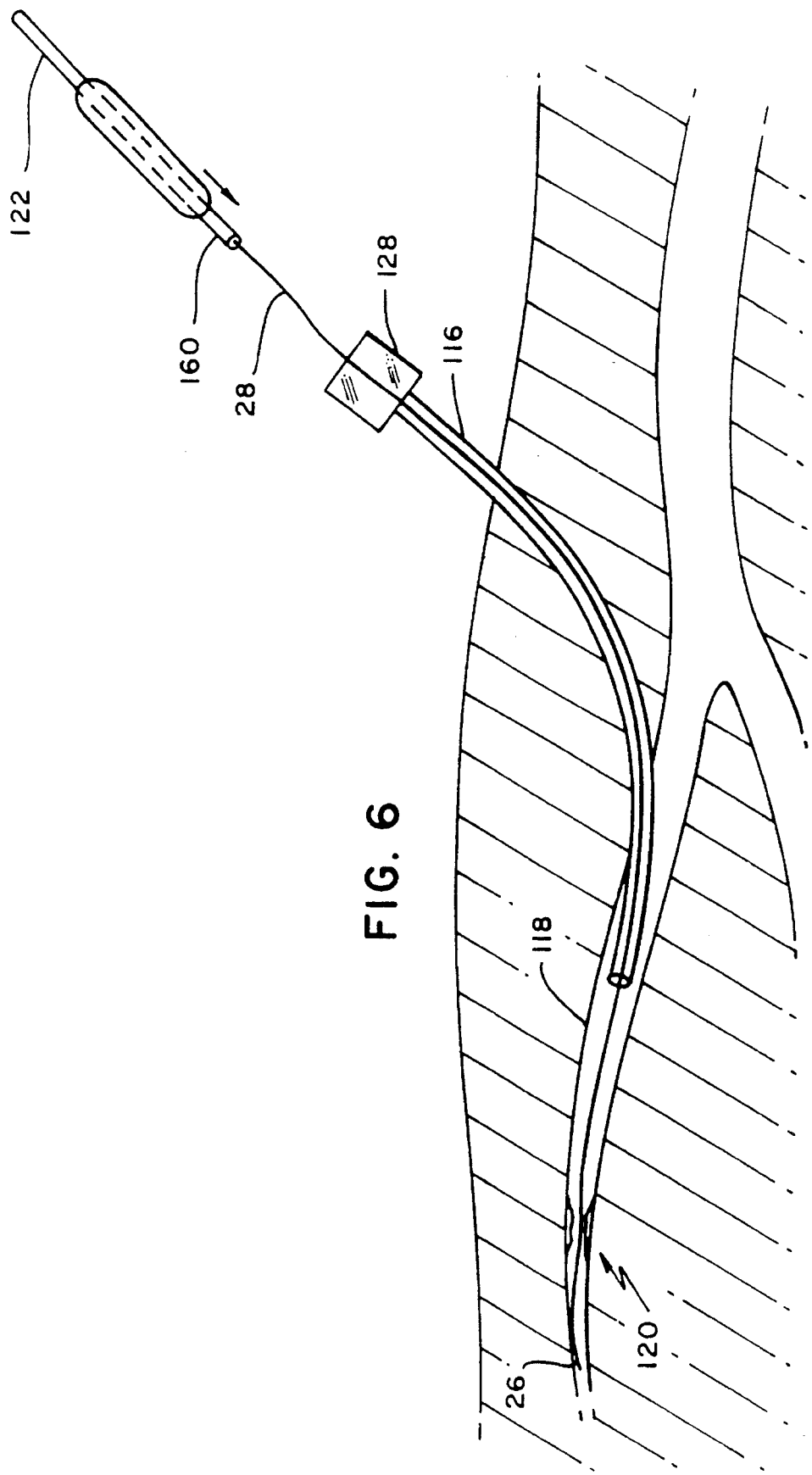

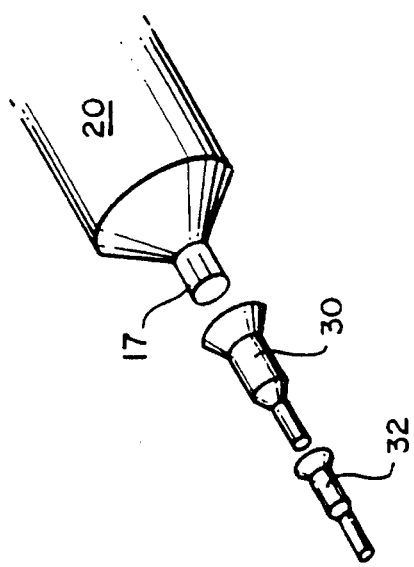
FIG. 6a
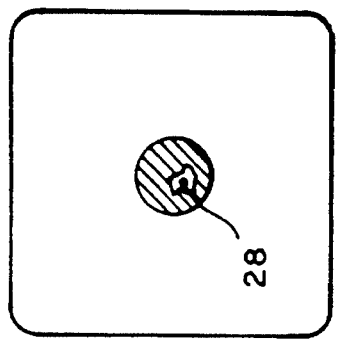
FIG. 6b
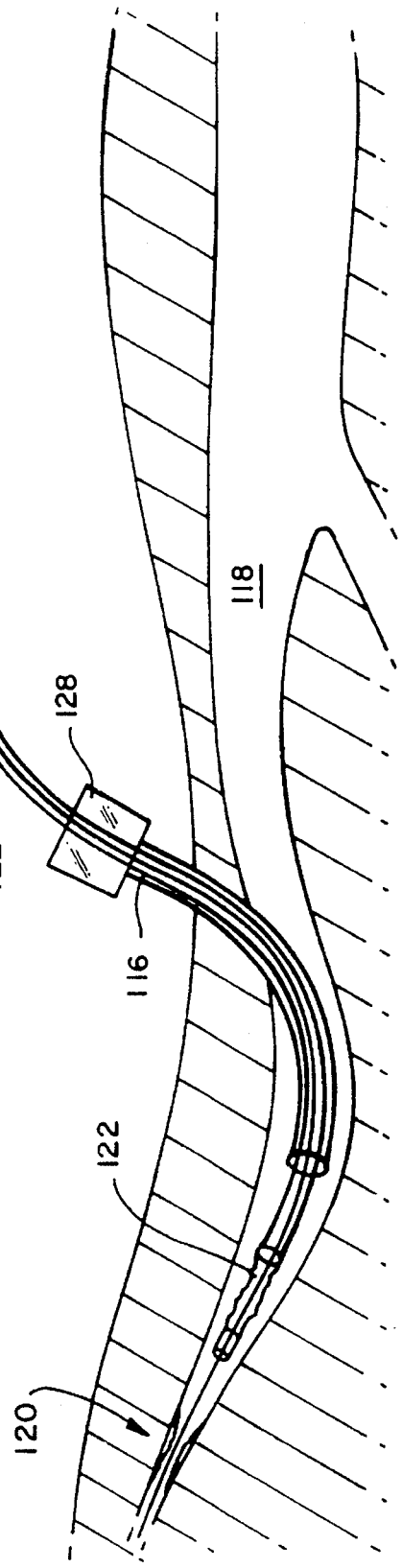

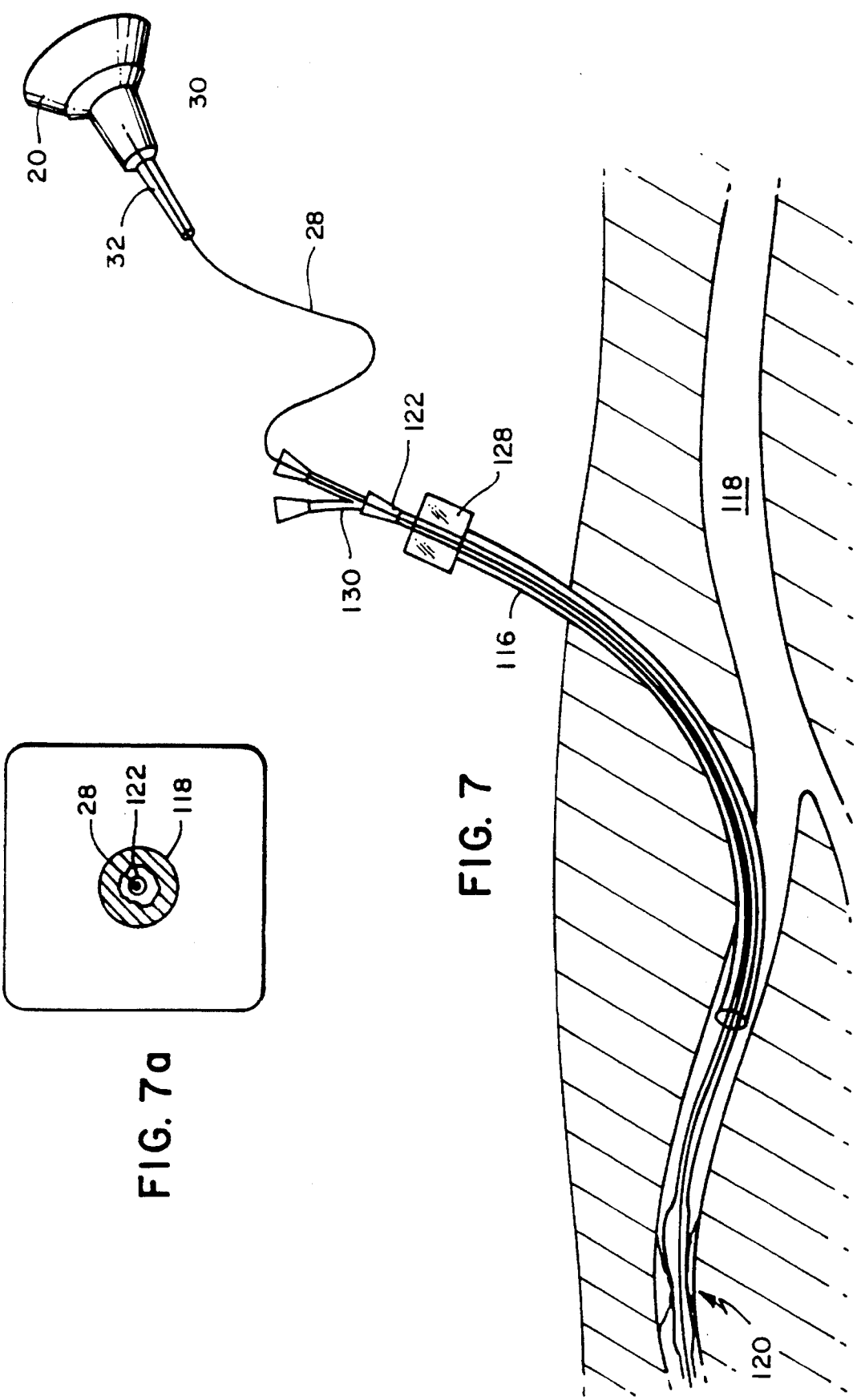

ULTRASOUND IMAGING GUIDEWIRE

RELATED APPLICATIONS

This application is a continuation of U.S. application Ser. No. 07/946,809, filed Sept. 17, 1992 by Mark A. Hamm et al. and now U.S. Pat. No. 5,368,035, which is a continuation of U.S. application Ser. No. 07/839,178, filed Feb. 21, 1992 by Mark A. Hamm et al. and now abandoned, which is a continuation-in-part of U.S. application Ser. No. 570,319, filed Aug.21, 1990, by Robert J. Crowley et al. and entitled: "Acoustic Imaging Catheter and the Like and now abandoned."

BACKGROUND OF THE INVENTION

This invention relates to medical guidewires typically used by physicians to gain access to restricted regions of the body and over which therapeutic devices such as small-diameter interventional catheters are threaded for insertion to a point of interest. The invention also relates to acoustic imaging within the body employing a rotating transducer arrangement.

It has long been recognized that acoustic imaging by a catheter containing a rotating transducer is useful in visualizing conditions of the body. It has been obvious that a therapeutic device, if sufficiently large, could be slid over such a catheter for insertion to a point of interest. However, practical features have not been available to enable realization of an acoustic guidewire, i.e., a true guidewire that contains a rotating transducer and which simultaneously provides the hand with the feel and torquability of a typical guidewire for enabling introduction of small-diameter therapeutic devices in typical guidewire fashion, and which also has a useful acoustic imaging capability.

SUMMARY OF THE INVENTION

The present invention provides features that enable the achievement of a practical acoustic guidewire.

In a first aspect, the invention provides a medical guidewire having a substantially uniform small diameter throughout its length and incorporating means for lateral acoustic scanning. The guidewire comprises a proximal connector, an extended main guidewire body portion, an axially elongated transition section, and a floppy tip portion, the main body portion comprises a stationary outer wall including means capable of transmitting torque and, within the outer wall, an elongated rotatable shaft with a distally positioned acoustic imaging transducer mounted thereon, the proximal connector is constructed to be attached to and detached from a drive device to enable a therapeutic device to be introduced over the guidewire, the connector has a stationary portion secured to the outer wall and an inner drive portion secured to the shaft, the floppy tip portion comprises an outer wire coil and a core rod which tapers from a relatively large diameter at a proximal joint with the outer wire coil to a floppy distal tip, and the elongated transition section serves to join the main body portion to the floppy tip section in a manner retaining substantially the same lateral stiffness as the main body portion and sufficient torquability to enable torquing of the floppy tip by torque applied to the proximal end of the guidewire.

In various preferred embodiments, the transition section, which joins the main body portion and the floppy tip portion, comprises an axially elongated central member joined to one of the portions and the central member interfits with running clearance with an outer member joined to the other portion, while substantially the full length of the transition section is occupied by structure that imparts lateral stability to render the transition section kink-resistant. Preferably, the central member is an elongated extension that extends distally to an end immediately adjacent to the joint of the core rod of the floppy tip portion to the outer wire coil of the floppy tip portion. In one preferred embodiment of this aspect, the central member of the transition section comprises a proximal extension of the core rod of the floppy tip portion, preferably, the transducer is disposed in a housing, rotatable with the rotatable shaft, which carries at its distal end a member having a central bore, and the proximal extension of the core rod of the floppy tip extends proximally through the bore and is joined to a retainer element within the housing proximal of the bore.

In another preferred embodiment of this aspect, the stationary outer wall of the main body of the guidewire includes a torsion-transmitting multifilar helical coil, a distal portion of the coil extends over the region occupied by the rotatable transducer, the filaments of the coil in the region are substantially spread apart for providing a substantially sonolucent window for the transducer, and extremities of the filaments of the coil located distally of the transducer are secured to transmit torque to the floppy tip portion. In another preferred embodiment of this aspect, the connector includes an electrically conductive grounded shaft stub secured to a coil of the rotatable shaft. In another preferred embodiment of this aspect, the proximal connector is a mini-connector of substantially the same diameter as the main body guidewire portion, and a proximal extension of at least the outermost part of the stationary outer wall of the main guidewire body portion extends over and joins to the mini-connector.

In another preferred embodiment of this aspect, the elongated rotatable shaft has a radial dimension sufficient to provide radial support to the outer wall to prevent kinking thereof. In another preferred embodiment of this aspect, the rotatable transducer is distally supported by an elongated laterally load bearing trunnion, to permit a lateral load to be uniformly transmitted through and from the transition section.

In another aspect, the invention features a medical guidewire incorporating means for lateral acoustic scanning. The guidewire comprises an extended main guidewire body portion, an axially elongated transition section and a floppy tip portion, the main body portion comprises a stationary outer wall including means capable of transmitting torque and, within the outer wall, an elongated rotatable shaft with a distally positioned acoustic imaging transducer mounted thereon, the elongated transition section serving to join the main body portion to the floppy tip section in a manner retaining substantially the same lateral stiffness as the main body portion and sufficient torquability to enable torquing of the floppy tip by torque applied to the proximal end of the guidewire, and the transition section, which joins the main body portion and the floppy tip portion, comprises an axially elongated central member joined to one of the portions, the central member interfits with running clearance with an outer member joined to the other portion, substantially the full length of the transition section is occupied by structure that imparts lateral stability to render the transition section kink-resistant.

In various preferred embodiments, the central member of the transition section comprises a proximal extension of a core rod of the floppy tip portion, preferably, the transducer is disposed in a housing rotatable with the rotatable shaft and the housing carries at its distal end a member having a central bore, and the proximal extension of the core rod of the floppy tip extends proximally through the bore and joins to a retainer element within the housing proximal of the bore.

In one preferred embodiment of this aspect, the central member is an elongated extension which extends distally to an end immediately adjacent to a joint with an outer wire coil of the floppy tip portion. In another preferred embodiment of this aspect, the stationary outer wall of the main body of the guidewire includes a torsion-transmitting multifilar helical coil, a distal portion of the coil extends over the region occupied by the rotatable transducer, the filaments of the coil in the region are substantially spread apart for providing a substantially sonolucent window for the transducer, and extremities of the filaments of the coil that are located distally of the transducer are secured to transmit torque to the floppy tip portion.

In another aspect, the invention features a medical guidewire incorporating means for lateral acoustic scanning. The guidewire comprises an extended main guidewire body portion, and a floppy tip portion, the main body portion comprises a stationary outer wall including means capable of transmitting torque and, within the outer wall, an elongated rotatable shaft with a distally positioned acoustic imaging transducer mounted thereon, and the stationary outer wall of the main body of the guidewire includes a torsion-transmitting multifilar helical coil, a distal portion of the coil extending over the region occupied by the rotating transducer, the filaments of the coil in the region are substantially spread apart for providing a substantially sonolucent window for the transducer, and extremities of the filaments of the coil that are located distally of the transducer are secured to transmit torque to the floppy tip portion.

In various preferred embodiments, the filaments have a pitch angle of the order of 45° in the region in registry with the transducer. In one preferred embodiment of this aspect, the helical coil is comprised of at least 3 filaments, the axial width of each of which, in the region in registry with the transducer, is about ⅓ or less of the corresponding dimension of the aperture of the transducer so that a substantial portion of the aperture is unobstructed at any point during rotation of the transducer, preferably the portion of the coil in the region of the transducer has an anti-echoic coating, and preferably the portion of the coil in the region of the transducer has a convex contour directed inward toward the transducer.

In another preferred embodiment of this aspect, the portion of the coil in the region of the transducer has an anti-echoic coating. In another preferred embodiment of this aspect, the portion of the coil in the region of the transducer has a convex contour directed inward toward the transducer. In another preferred embodiment of this aspect, the filaments of the torsion-transmitting coil of the wall of the guidewire, distal of the transducer have a smaller pitch angle so that turns of the coil which are closer together than the coil turns in registry with the transducer provide the extremities that are joined to the floppy tip portion.

In another aspect, the invention features a guidewire having a substantially uniform diameter throughout is length and incorporating means for lateral acoustic scanning. The guidewire comprises a proximal connector portion, an extended main body portion, an axially elongated transition portion, and a floppy tip portion, the main body portion is substantially hollow and has a torque transmitting winding therearound, which winding extends from the proximal portion across the transition portion containing an acoustic scanning means and attaches to the floppy tip portion for full torque transmission from the proximal end to the distal end of the guidewire.

In various preferred embodiments, the torque transmitting winding is a woven braid. In one preferred embodiment of this aspect, the transition portion includes a window opening for receipt of acoustic transmission fluid.

One advantage of the invention is improved dilatation procedures such as angioplasty by ultrasonic viewing of a body lumen with a guidewire to locate the region to be treated, to position properly a balloon catheter, and then to observe continuously the occluded region as the angioplasty procedure progresses. After treatment, the treated region of the body lumen could be inspected to determine the efficacy of the procedure. It is therefore one object of this invention to provide a guidewire having an ultrasonic probe.

Other aspects, features, and advantages of the invention will be apparent from the following description of the preferred embodiments and from the claims.

DESCRIPTION OF THE PREFERRED EMBODIMENT

The Figures will first briefly be described.

Drawings FIG. 1 is a view in partial cross-section of an ultrasound imaging guidewire attached to a driver;

Figure 2:
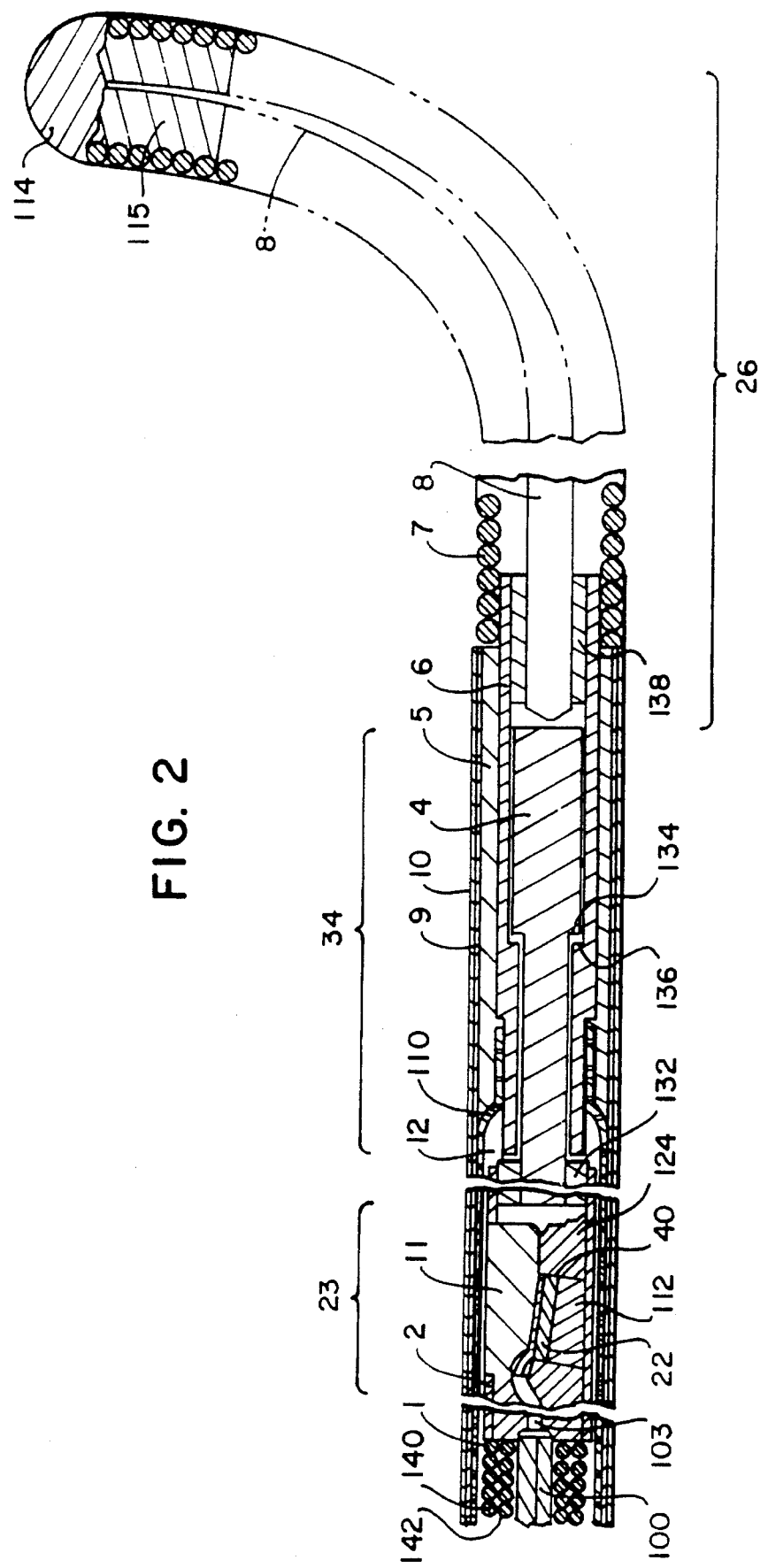
FIG. 2 is an enlarged cross-section side view of the distal end of the ultrasonic guidewire.
Figure 2A:
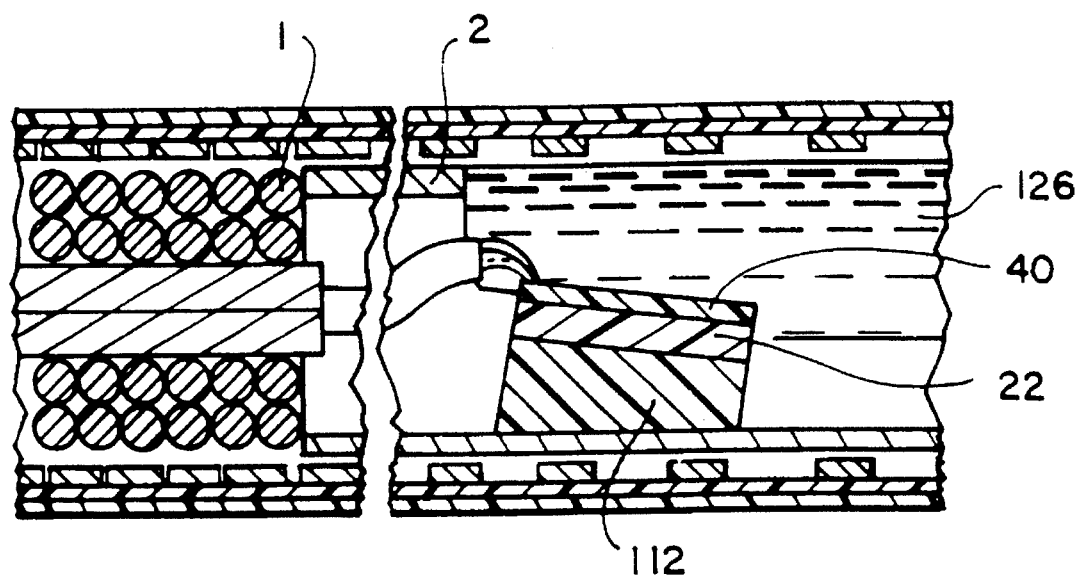
FIG. 2a is an alternate transducer assembly.
Figure 2B:
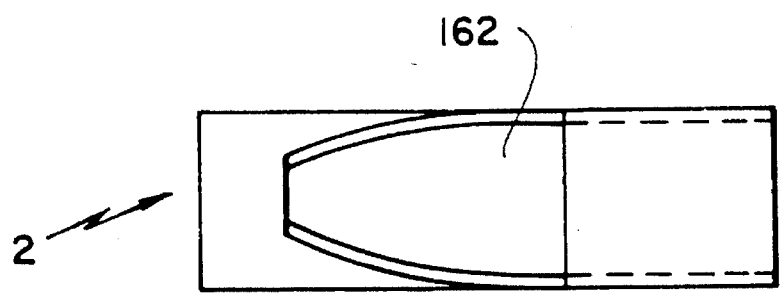
Figure 2C:
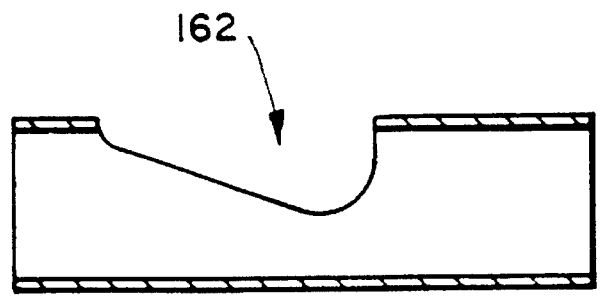
Figure 2D:
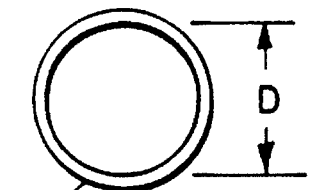
Figure 2E:
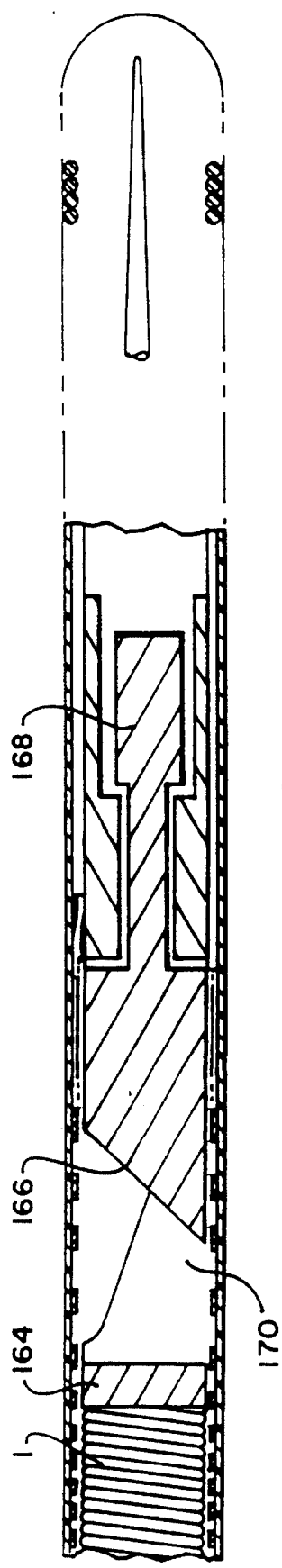
Figure 2F:
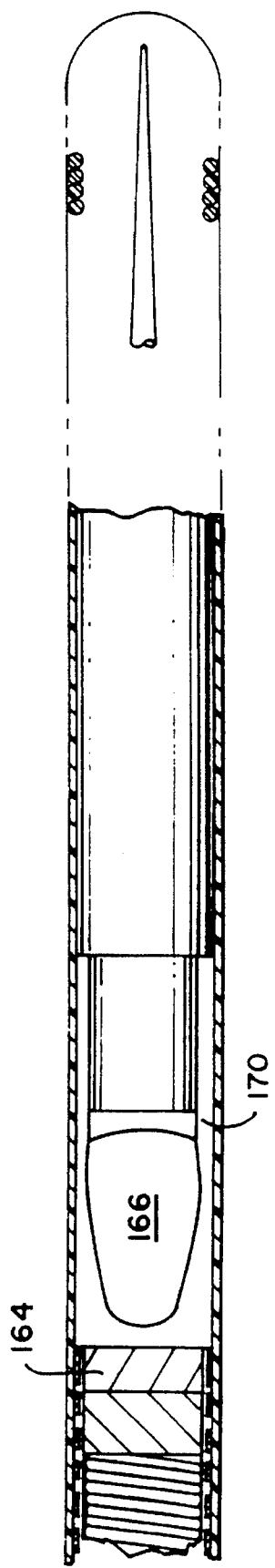
Figure 2G:
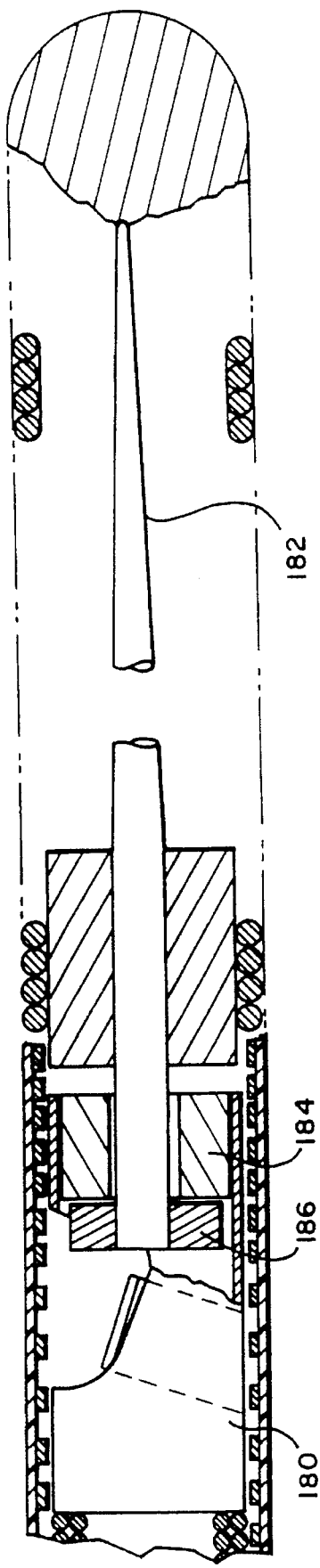
Figure 2H:
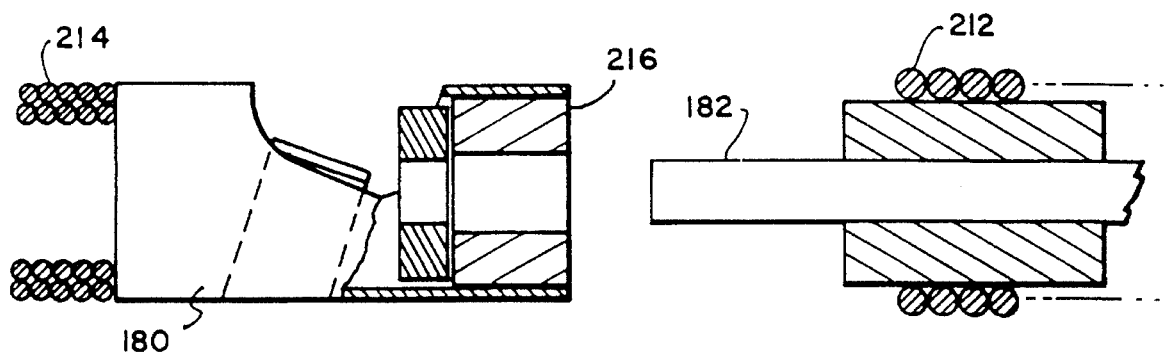
Figure 2I:
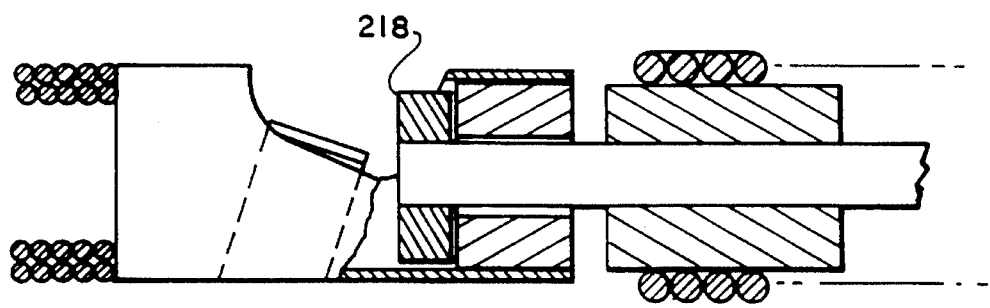
Figure 2J:
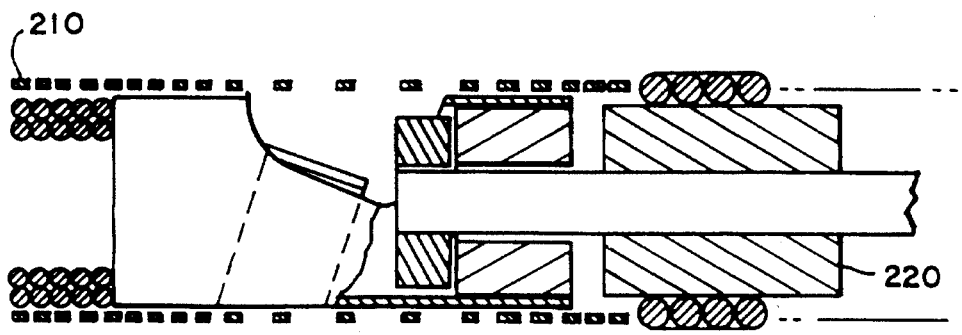
Figure 2K:
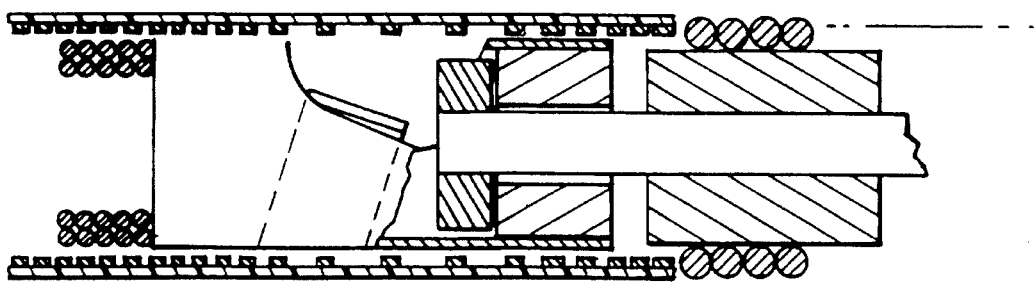
Figure 3:
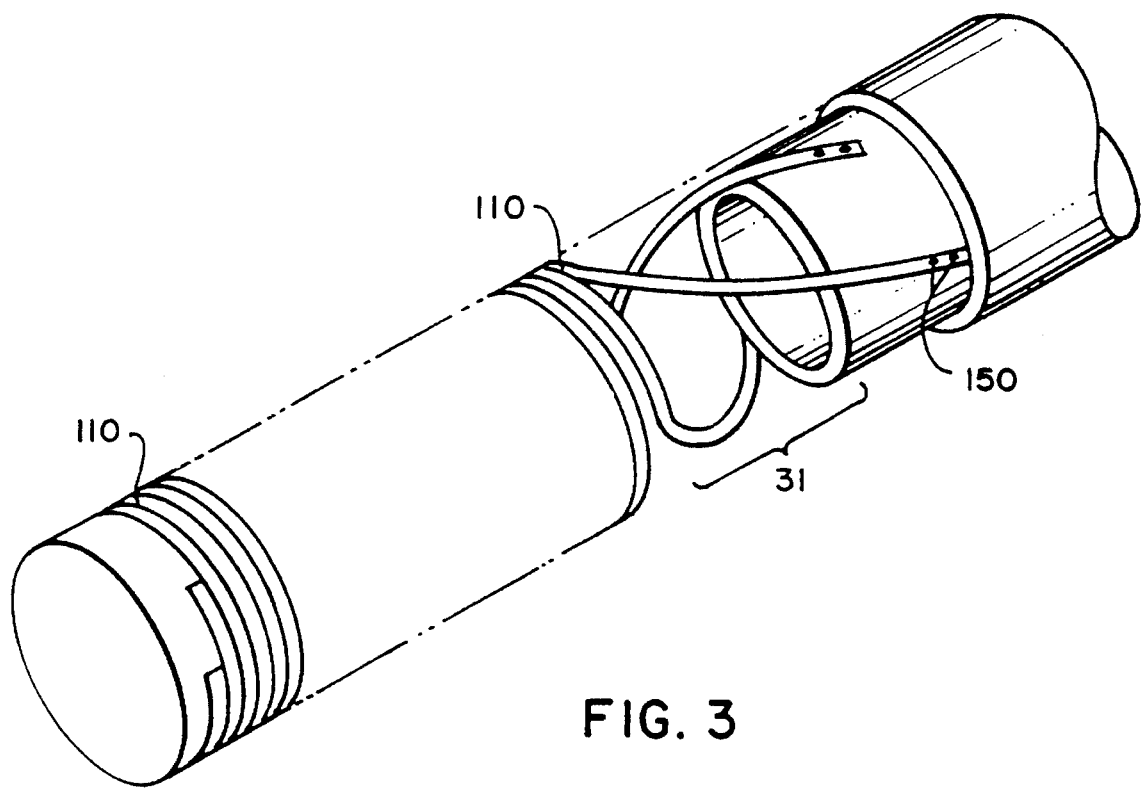
Figure 8A:
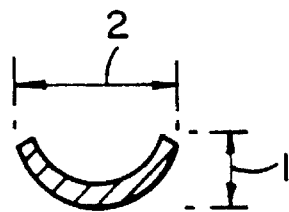
Figure 8B:
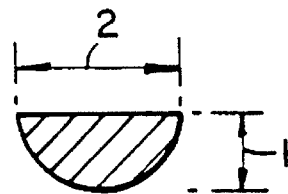
Figure 8:
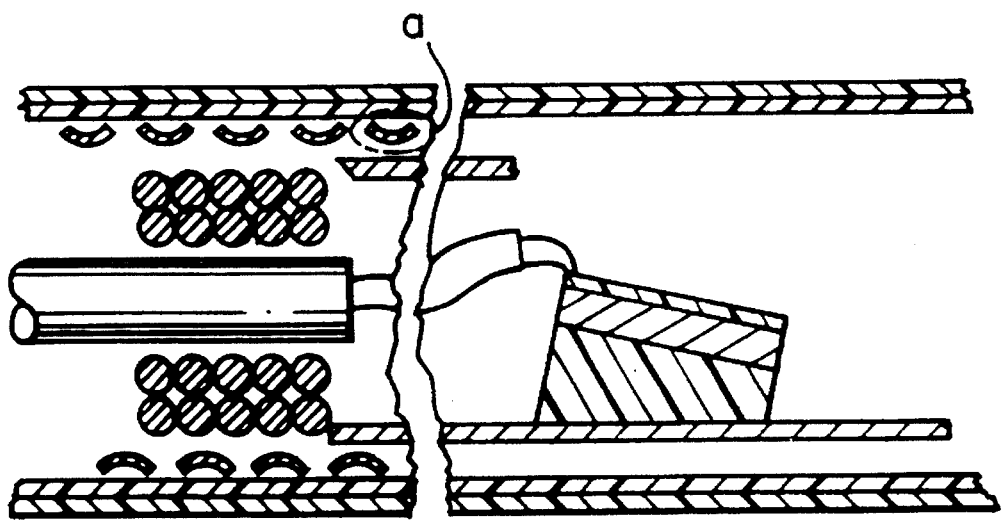

FIGS. 2b, 2c, and 2d are views of a transducer housing;

FIG. 2e is a cross-section view of a transducer assembly employing a mirror;

FIG. 2f is a plan view of the transducer assembly of FIG. 2e;

FIG. 2g is a cross-section view of an embodiment having a different transition section;

FIGS. 2h, 2i, 2j, and 2k show a method of assembly of the embodiment of FIG. 2g, FIGS. 2j and 2k also show an embodiment in which the flat wires rejoin after the window area;

FIGS. 2l, 2m, 2n, 2o, and 2p show a method of assembly of an ultrasonic guidewire similar to that shown in FIG. 2, FIGS. 2o and 2p also show an embodiment in which the flat wires of the coil layer rejoin after the window area;

FIG. 3 is a perspective view of the region adjacent the transducer assembly and the transducer assembly, with polymeric outer layers removed;

FIGS. 4, 5, 5a, 6, 6a, 6b, 7, and 7a show, in sequence, a method of using the ultrasound imaging guidewire in the body; and FIGS. 8, 8a, and 8b are views in cross-section of an alternate type of flat wire useful in forming a wound coil layer.

GENERAL DESCRIPTION

Figure 1:
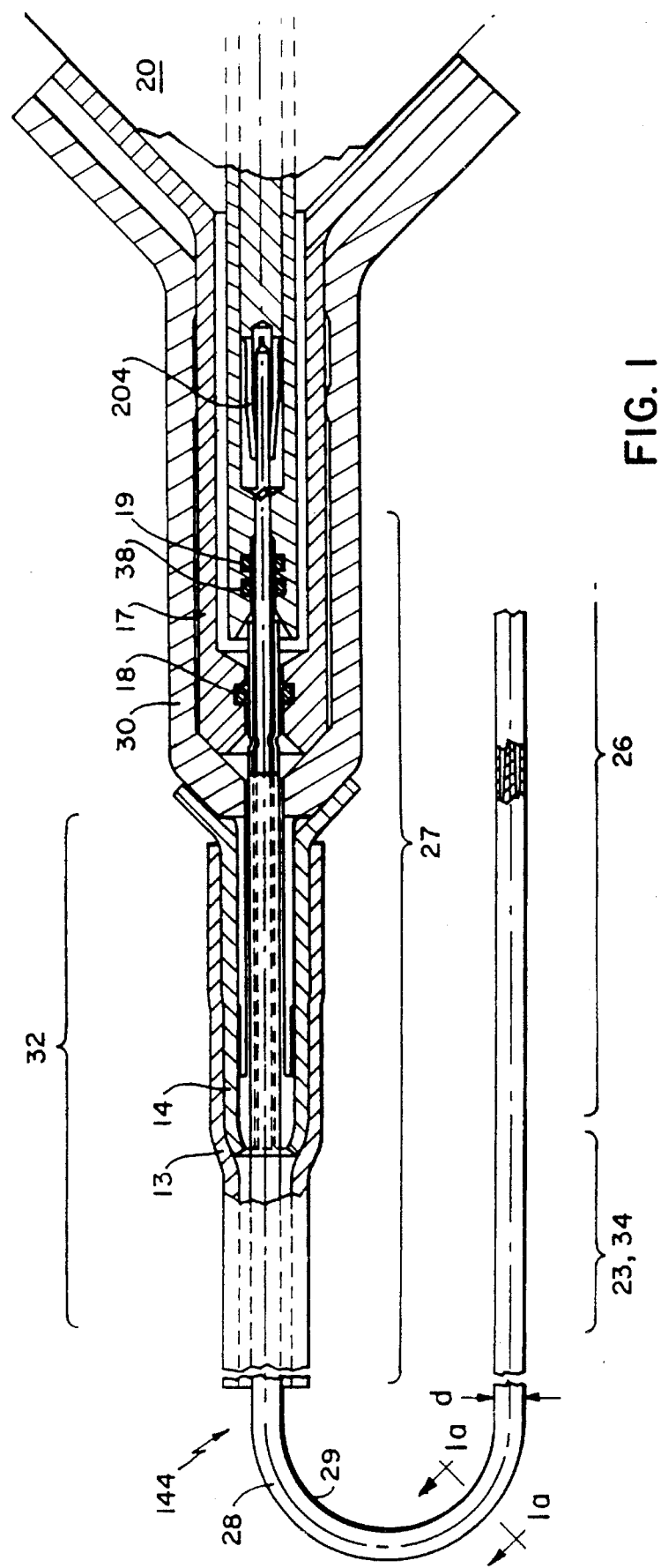
FIG. 1a is an end-on cross-section along the line 1a–1a in FIG. 1.
FIG. 1b is a view in partial cross-section of a mini-connector attached to the proximal end of the ultrasonic guidewire.

The invention is a guidewire capable of obtaining ultrasonic images during use in narrow, tortuous body lumens. Like conventional guidewires which do not enable acoustic imaging, a guidewire according to the present invention features a unitary structure with a uniform small diameter, d, along the main body 144 to a distal end (FIGS. 1 and 2). The main body exhibits uniform, suitable axial and lateral stiffness and torquability up to a desired distal region beyond the ultrasonic transducer, where the stiffness predictably gradually changes to a floppy tip 26 so that the guidewire enables predictable torquing and pushability from proximal regions to the distal tip as is required for proper functioning as a guidewire. After placement of the guidewire in the body, a medical treatment device, such as a dilatation catheter can be slipped over the guidewire for positioning at a site of intended use (FIG. 4 et seq). At the same time, the guidewire of the invention allows the user to obtain 360° acoustic images of the lumen wall to, for example, determine the state of a site of interest, position the medical treatment device, monitor the progress of treatment and observe the site after treatment to determine the course of further treatment.

The invention achieves these features despite inherent limitations of rotary acoustic imaging systems, such as the requirement for a central lumen through the body of the device for the coaxial cable and the need for a sonolucent window to allow lateral passage of the ultrasonic energy. In preferred embodiments, the guidewire is comprised of an outer tubular wall member 29 formed of a sonolucent polymeric material, that incorporates for reinforcement, a multifilar helical coil 110, extending the length of the main guidewire body and connected to the floppy tip to transmit torque and provide security in the region distal of the transducer assembly 23. The structure provides a sonolucent window region 31 by spreading apart of the wire coils of the outer wall, at a pitch angle (an angle of turn referenced to the normal to the longitudinal axis of the ultrasonic guidewire), e.g., between about 30° to 45°, that still enables torque transmission over the region corresponding to the transducer position (FIG. 3). Also, the wire width is preselected such that it is small compared to the transducer aperture size to thus minimize the percentage of the acoustic beam blocked by the wires as the transducer rotates beneath them. In preferred embodiments, the side of the wires facing the transducer are convex in cross-section and/or coated with an anti-echoic material (FIG. 8).

Cooperating with the structure of the outer tubular member is substantially continuous central core structure, formed by different components at different points along the length, occupying substantially the cross-section of the guidewire throughout the main guidewire body and distal of the transducer through an elongated transition region which joins the main guidewire body to the floppy tip. This core structure enhances lateral and axial stiffness, and minimizes the possibility of kinking of the thin outer wall member. In portions of the guidewire proximal to the transducer, the core preferably includes a rotatable, counter-wound multifilar drive shaft connected to the transducer housing. Distal to the rotatable transducer housing is an extension, also substantially occupying the inner lumen, extending to the floppy tip. The floppy tip has a tapered core rod that extends to the most distal tip of the guidewire. In one embodiment, the extension from the transducer is a distal rotatable extension fixed to the transducer housing which connects to the floppy tip through a rotatable joint (see e.g., FIG. 2). In another embodiment, the core rod of the floppy tip extends proximally to and interfits with the transducer housing in a rotatable joint configuration (e.g., FIG. 2g). In either case, the floppy tip is effectively connected to the transducer housing, with the transition region containing a substantially continuous core structure. In the floppy tip region, the core structure is connected to the outer wall member, including the wire coils, to form a unitary structure which contributes to the desirable flexural and torque-transmitting characteristics mentioned above.

Figure 1A:
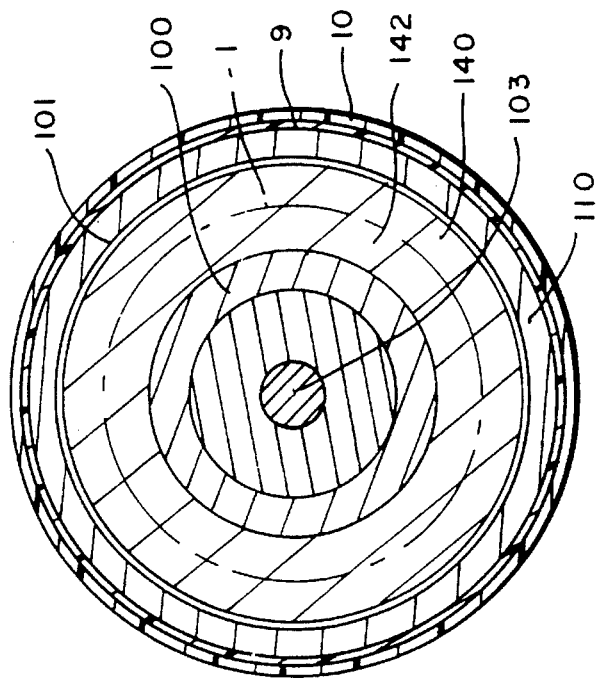
Figure 1B:
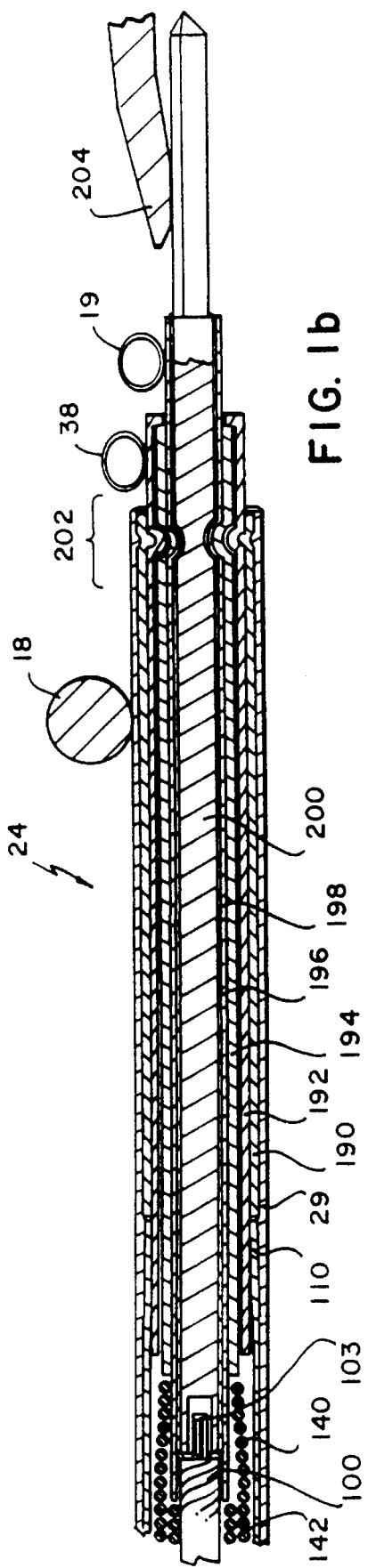

At the most proximal portion of the guidewire, a connector structure of the same diameter as the main body of the guidewire is provided that enables demateable connection of the wire to an ultrasonic driver for obtaining ultrasonic images (FIG. 1b). The structure provides a small outer diameter so that, upon disconnection, the medical treatment device, such as a balloon catheter with a guiding lumen diameter having substantially the same diameter as the guidewire, can be slipped over the guidewire and positioned within the body. At the same time, this mini-connector structure allows for rotation and control of the transducer through the driver.

Structure

Referring to FIGS. 1 and 2, an ultrasound imaging guidewire 28 includes a proximal end portion 27 adapted for coupling to an ultrasonic drive 20, a main guidewire body portion 144 which houses a miniature, rotatable transducer assembly 23 and its drive shaft, an elongated transition section 34 distal of the transducer containing a core structure, and a floppy tip assembly 26 secured to the outer wall of the main guidewire body. The guidewire body portion 144 has a small maximum outside diameter d (e.g., about 0.025 inch). The overall length of ultrasonic guidewire 28 is between approximately 120 to 180 cm, preferably about 160 cm. The outside diameter is substantially constant along the length, and generally not greater than the body 144, to the distal tip of floppy tip assembly 26 which has an outside diameter of about 0.025.

Floppy tip assembly 26 is about 10 cm in length, transition section 34 is between about 2 to 4 cm long, and transducer assembly 23 is between about 3 to 5 mm in length. Thus, assemblies 26, 34, and 23 together constitute between about 7 to 12% of the total length of ultrasonic guidewire 28.

The guidewire body is adapted for passage through a long, narrow body lumen such as a restricted, tortuous blood vessel. The main guidewire body is comprised of an outer tubular wall member 29 in which miniature, relatively rotatable ultrasonic transducer assembly 23 is disposed for 360° rotational scanning of the lumen wall surrounding the transducer assembly 23. A sonolucent window area 31 (see FIG. 3) surrounds transducer assembly 23 and allows ultrasonic energy emitted by transducer assembly 23 to escape from ultrasonic guidewire 28. A narrow (e.g., 0.017 inch), tubular, rotatable inner drive shaft 1 (also see FIG. 1a) rotates transducer assembly 23, and a detachable driver 20 rotates drive shaft 1. Drive shaft 1 is a multi-filar system formed of two counter-wound layers of helically wound round wire 140, 142. Each round wire 140, 142 has an outside diameter of about 0.0025 inch. Drive shaft 1 is torsionally stiff but flexible enough laterally to follow the path of a narrow, tortuous blood vessel. A further description of a drive shaft of this general type is contained in U.S. Pat. No. 4,951,677 and in U.S. patent application Ser. No. 570,319 (filed Aug. 21, 1990 and commonly owned with the present application), which are both incorporated herein by reference. With ultrasonic guidewire 28 inserted into a particular lumen of a patient's body, rotation of transducer assembly 23 by driver 20 connected to an ultrasonic control system (not shown) allows real-time, 360° ultrasonic images to be obtained of the body lumen. The control system processes data supplied by rotating transducer assembly 23 and displays real-time ultrasound images on a display device (not shown).

Ultrasonic guidewire 28 is constructed to have stiffness and torqueability characteristics that allow ultrasonic guidewire 28 to be positioned in the body by standard guidewire procedures, for example, within a blood vessel or the heart by guiding the flexible guidewire through various blood vessels along a circuitous path, starting, for example, by percutaneous introduction through an introducer sheath (see FIG. 4). Drive shaft 1 and outer tubular wall member 29, as well as the transition section 34, are constructed to cooperate to provide uniform lateral stiffness along the length of the device to the floppy distal tip assembly.

Outer tubular wall member 29 of ultrasonic guidewire 28 is sonolucent and includes an inner polymeric layer 9 and an outer polymeric layer 10 (also see FIG. 1a). Outer polymeric layer 10 is formed of a sonolucent material such as nylon or its equivalent. A requirement for outer layer 10 is that it must enable a therapeutic device such as a standard balloon dilatation catheter to slide freely over its exterior surface. Inner polymeric layer 9 is cross-linked polyethylene that provides acoustic matching and strength. Inner layer 9 may be coated (e.g., by vacuum depositing) on its exterior and/or interior with a thin (e.g., 1500 Angstroms) layer of metal, such as aluminum, to form an EMI/RFI shield. The overall thickness of outer tubular wall member 29 is approximately 3 mils (i.e., 0.003 inch) with outer layer 10 being approximately 1 mil and inner layer 9 being about 2 mils thick.

To enhance lateral stiffness and torqueability, a reinforcing coil layer 110 (also see FIGS. 1a and 3) is associated with outer tubular wall member 29, preferably consisting of a single thickness of three separate helically and adjointly wound flat wires disposed within and bonded (e.g., by a hardenable bonding material such as epoxy) to outer tubular member 29 of ultrasonic guidewire 28. (In other embodiments, as described below, the helical coil may be non-bonded and biased outwardly against inner and outer polymeric layers 9 and 10. This is described fully below.) Wound flat wire coil layer 110 provides RF shielding and therefore it is generally not necessary to coat inner layer 9 with a thin layer of metal, as mentioned previously. A running clearance 101 (e.g., 0.0015 inch) is provided between wound flat wire coil layer 110 and the outer round wire 140 of drive shaft 1 (as shown in FIG. 1a). Wound flat wire coil layer 110 also provides the main torquability, uniform lateral stiffness, and columnar strength qualities desired in a guidewire that is inserted by application of axial thrust and torquing motions from the proximal end. Wound flat wire coil layer 110 transmits the axial force and torque down the length of ultrasonic guidewire 28. Bonding coil layer 110 to outer tubular member 29 (or, alternatively, biasing coil layer 110 against outer tubular member 29) prevents unwinding or winding together of the coils thus enabling torque to be transmitted when ultrasonic guidewire 28 is torqued in either the clockwise or counterclockwise direction. The individual flat wires that form coil layer 110 along the main body of the guidewire are wound such that lateral stiffness and torqueability is enhanced while the guidewire remains flexible enough to follow a tortuous path with a body lumen. Each flat wire is approximately 2 mils by 5 mils (i.e., 0.002 inch by 0.005 inch) in cross section and is formed from metal (e.g., stainless steel). Thus, wound flat wire coil layer 110 has a radial thickness of about 0.002 inch. In the region of the transducer, the three individual flat wires of coil layer 110 are wound at a pitch angle (an angle of turn referenced to the normal to the longitudinal axis of the ultrasonic guidewire) which is typically between about 30° to 45° greater. That is, the three wires are circumferentially spaced apart to form window area 31 around the transducer so that acoustic energy can escape. At the distal end, the flat wires are spot welded at points 150 to the proximal end of a stepped stainless steel cylinder 6 (formed of hypotube) in the transition section 34 to transmit torque to the more distal portions of ultrasonic guidewire 28 (FIGS. 2 and 3).

The transition section includes an elongated extension of the rotating assembly in the form of an elongated trunnion 4 (e.g., made of stainless steel or nitinol) and the interfitting cylinder 6, and is formed from a section of hypotube designed to provide tensile strength and lateral stiffness at the transition between transducer assembly 23 and floppy tip assembly 26, and to transmit torque to the floppy tip assembly while at the same time allowing transducer assembly 23 to rotate. It is also designed to shift an axial tensile load applied to the floppy tip which exceeds the limits of outer tubular member 29 and wound flat wire coil layer 110 to drive shaft 1. The cylinder 6 is preferably short in length, e.g., less than 1 cm (preferably 1 to 5 mm), to avoid excessive stiffness in the transition section 34 to promote general uniformity of lateral stiffness along the guidewire. The smaller inner diameter portion of cylinder 6 is about 0.3 mm, and the larger inner diameter portion measures about 0.35 mm.

At its proximal end, the elongated trunnion 4 is joined, for example by spot welding, to a hypotube spacer 132 which in turn is joined, for example by spot welding, to a generally tubular stainless steel housing 2 of transducer assembly 23. Thus, elongated trunnion 4 rotates with transducer assembly 23 within relatively non-rotatable cylinder 6 joined to the outer tubular wall member 29 of the main body of the guidewire and to the floppy tip assembly. Elongated trunnion 4 acts as a stiffening core structure to prevent buckling of ultrasonic guidewire 28 in this region distal to transducer assembly 23. The thinner neck portion of elongated trunnion 4 has an outside diameter of about 0.010 inch while the thicker portion is about 0.012 inch in outside diameter.

A step 134 in elongated trunnion 4 opposes, with running clearance, a step 136 of cylinder 6 such that relative axial motion between floppy tip assembly 26, transducer assembly 23, and drive shaft 1 is allowed but significantly limited. Steps 134, 136 provide an abutting feature that prohibits substantial relative axial motion of the floppy tip thus securing it against loss, e.g., during withdrawal of the guidewire from a body lumen, while allowing rotational movement of the transducer assembly. In normal use (e.g., when the parts are not pulled axially apart beyond the tensile strength of outer tubular member 29), the running clearance provided between step 134 and step 136 is large enough to allow free rotation (e.g., about 0.0005 to 0.001 inch). Also, during normal use, a gap large enough to allow free rotation (e.g., about 0.0005 to 0.001 inch) is provided generally between elongated trunnion 4 and cylinder 6 (this gap is not clearly shown in the drawings), and a teflon-impregnated coating, such as anodize or nickel plate, is applied to the exposed surfaces of elongated trunnion 4 to help reduce friction if engagement occurs during rotation. Sonolucent fluid 12 (e.g., silicone oil) fills the gap between elongated trunnion 4 and cylinder 6. As described previously, transition section 34 is between about 2 to 4 cm in length, and is a relatively stiff region designed to shift, to drive shaft 1, a tensile load between the floppy tip assembly and the main body of the guidewire which exceeds the limits of outer tubular member 29 and wound flat wire coil layer 110 to drive shaft 1.

In securing cylinder 6 to the floppy tip assembly, cylinder 6 is attached, for example by spot welding, to a hypotube spacer 138 which is connected, for example by spot welding, to a tapered, flexible core rod 8 inside of non-rotating floppy tip assembly 26. Core rod 8 has a maximum diameter of about 10 mils at its proximal end and tapers down gradually along its length to a diameter of about 3 mils at the distal end of floppy tip assembly 26. Floppy tip assembly 26 includes a member 115 surrounding core rod 8 at the distal end of core rod 8. Member 115, which is a material such as hard solder or braise, is about 2 to 3 mm in length. One end of member 115 abuts a ball 114 (described below). Floppy tip assembly 26 also includes an outer floppy layer 7 of a helical coil of round wire, the coil having an outside diameter of about 0.025 inch and being spot welded to the distal end of cylinder 6. The transition section 34 therefore also plays an important safety role in that loads are transferred to the wound flat wire coil layer 110, which is connected to the floppy tip assembly 26 through transducer assembly 23 and transition region, to reduce the likelihood that the floppy tip assembly 26 will separate from the rest of ultrasonic guidewire 28 when ultrasonic guidewire 28 is pushed, pulled, or rotated while in the body.

The round wire used to form outer floppy layer 7 has an outside diameter of approximately 0.0035 inch. The distal end of floppy tip assembly 26 includes a ball 114 welded and braised to the round wires as well as to the distal tip of core rod 8. Floppy tip assembly 26 is designed to be a soft, pliable, non-rotatable tip which can easily follow the path of a body lumen. The lateral stiffness of floppy tip assembly 26 gradually decreases from its connection to transition section 34 to ball 114 at its other end. The lateral stiffness at the end of floppy tip assembly 26 is substantially less than the uniform lateral stiffness exhibited by the main section of the guidewire body (i.e., the section surrounded by wound flat wire coil layer 110 including the transition section 34).

As seen best in FIG. 3, sonolucent window area 31 surrounds transducer assembly 23 and allows ultrasound energy from transducer assembly 23 to be transmitted essentially unattenuated. As mentioned above, window 31 is formed by separating the individual flat wires from wound flat wire coil layer 110 and extending them in a somewhat longitudinal direction in window area 31 to a lead angle of the order of 45°. Referring to FIG. 2, the ends of the flat wires are spot welded to stepped cylinder 6 which is a component in the transition section 34. The ends of the individual flat wires are also held in place against the outer tubular wall member 29 by, for example, epoxy 5.

Because the individual flat wires which form coil layer 110 separate in window area 31 and because an approximately 2 to 3 mil running clearance is provided between the generally cylindrical rotatable housing 2 and outer tubular wall member 29 in window area 31, window area 31 provides a relatively short (e.g., between about 3 to 5 mm) region. The transition section 34 acts to provide substantially uniform lateral stiffness throughout the length of ultrasonic guidewire 28.

As shown in FIGS. 2 and 3, transducer assembly 23 at the distal end of ultrasonic guidewire 28 includes a piezoelectric crystal (PZT) 22 inside of stainless steel housing 2. A solid couplant 11, preferably formed from a solid polymeric member (e.g., polystyrene), is also located inside housing 2. PZT 22 is bonded to a matching layer 40 which is, for example, a layer of conductive epoxy. The surface of matching layer 40 opposite PZT 22 is attached to solid couplant 11, and a backing layer 112 is attached to the surface of PZT 22 opposite matching layer 40. Backing layer 112 is formed from an acoustically absorbent material (e.g., an epoxy substrate having tungsten particles). Ultrasound energy is emitted from the PZT 22, passes through matching layer 40, and is launched by solid couplant 11. Matching layer 40 is designed to allow the ultrasound energy to pass substantially unattenuated from PZT 22, which has a relatively high acoustic impedance, to solid couplant 11, which has a comparatively low acoustic impedance. The ultrasound energy launched by solid couplant 11 passes through a thin layer of sonolucent fluid 12 such as silicone oil. The sonolucent fluid 12 fills a gap between solid couplant 11 and wound flat wire coil layer 110.

Referring to FIGS. 2b, 2c, and 2d, stainless steel housing 2 is generally cylindrical with an inside diameter D of about 0.015 inch and a wall thickness of about 0.002 inch, and includes an opening 162 to allow acoustic energy to escape. Solid couplant 11 is disposed adjacent to opening 162 such that acoustic energy always has a means of escape from housing 2 as it rotates. The width (e.g., 0.005 inch, as stated previously) of each of the widely separated flat wires that are helically coiled to form coil layer 110 of outer tubular wall member 29 (which is relatively stationary) is significantly less than the size of opening 162 (i.e., less than the acoustic aperture formed in the transducer housing) and therefore a flat wire in the window area 31 (see FIGS. 2 and 3) does not substantially interfere with or block the transmission of energy from opening 162 in rotating housing 2. The width of each flat wire is preferably about three or four times smaller than opening 162 (i.e., than the acoustic aperture of the transducer housing).

Turning now to FIG. 2, housing 2 is attached, for example by spot welding or butt welding, to drive shaft 1, and the entire transducer assembly 23 rotates with drive shaft 1. A center conductor 103 of an inner coaxial cable 100 electrically connects to transducer assembly 23 and thus allows PZT 22 to produce ultrasonic energy.

Referring to FIG. 2a, an alternate embodiment includes the use of a fluid 126 (e.g., water) instead of solid couplant 11 in the transducer assembly. In this embodiment, matching layer 40 is exposed directly to the fluid, but the remainder of the structure of the transducer assembly is similar to the embodiment previously described. Note that the running clearance between drive shaft 1 and wound flat wire coil layer 110 (i.e., running clearance 101 as shown in FIG. 1a) is exaggerated in FIG. 2a.

Referring to FIG. 1, the proximal end 27 (which is between about 1 to 2 cm in length) of ultrasonic guidewire 28 is connected to driver 20 by means of a collet assembly 32 and a sterile barrier 30. Collet assembly 32, which includes an elastic first tube 13 joined to an elastic second tube 14, acts together with sterile barrier 30 to provide a means of mechanically holding the proximal end of ultrasonic guidewire 28 connected to driver 20. A compression fit between collet assembly 32 and outer tubular member 29 provides mechanical holding of ultrasonic guidewire 28.

Referring to FIGS. 1 and 1b, the portion of proximal end 27 of ultrasonic guidewire 28 which extends into a nose 17 of driver 20 is mated (during assembly) with a mini-connector assembly 24 to facilitate electrical and driving connections from driver 20 to ultrasonic guidewire 28. Mini-connector 24 is an integral part of ultrasonic guidewire 28, and as such it remains in place after assembly at the factory (i.e., it is not designed to be removed by a user). The outside diameter of mini-connector 24 is effectively the same as the outside diameter of the ultrasonic guidewire itself, and while its length can vary widely, it is preferably between about 1 to 3 cm. As shown in FIG. 1b, mini-connector 24 includes (progressing from the outside inward)

a spacer layer 190 of polyethylene, a coil conductor layer 192 of copper, an outer insulator layer 194 of teflon, an outer conductor 196 of copper, an inner insulator 198 of nylon, and a solid conductor 200 of copper. The outermost layer is the outer tubular wall member 29 of the main body of ultrasonic guidewire 28, and is pulled over the mini-connector assembly (after the mini-connector is attached to the proximal end of the ultrasonic guidewire) and it covers the length of the mini-connector. Spacer layer 190 and coil conductor layer 192 are also designed to remain relatively stationary during operation, while outer insulator layer 194, outer conductor 196, inner insulator 198, and solid conductor 200 are designed to rotate with the rotatable parts of ultrasonic guidewire 28. A running clearance (not clearly shown in FIG. 1*b* because of its small size) of between about 1 to 2 mils is provided between coil conductor layer 192 and outer insulator layer 194 (i.e., at the boundary between rotating and stationary parts of mini-connector 24).

Mini-connector 24 is attached to the proximal end of ultrasonic guidewire 28 (at the factory) in the following manner. Rotatable solid conductor 200 is secured to center conductor 103 of inner coaxial cable 100 by, for example, conductive epoxy or solder. Rotatable outer conductor 196 is attached to the shielding of inner coaxial cable 100 and to both round wire coil layers 140, 142 of drive shaft 1 (e.g., by spot welding). Round wire layer 140 is proximally longer than layer 142 and is attached at a point proximal to round wire layer 142, as shown in FIG. 1*b*. Non-rotatable coil conductor layer 192 is secured to wound flat wire coil layer 110 by, e.g., spot welding. Outer tubular member 29 extends past the point of connection between the ultrasonic guidewire and the mini-connector and thus covers mini-connector 24.

With mini-connector 24 attached to ultrasonic guidewire 28, the proximal end of the ultrasonic guidewire is ready to be inserted into driver 20. When inserted into driver 20, an O-ring 18 disposed in driver nose 17 provides sealing. A canted coil spring 38, also disposed in driver nose 17, holds non-rotatable coil conductor layer 192, and thus wound flat wire coil layer 110, stationary and provides an electrical connection to coil layer 110 to channel any RF interference. Another grounded canted coil spring 19, also disposed in driver nose 17, connects to rotatable outer conductor 196 and thus transmits torque from driver 20 to drive shaft 1 and inner coaxial cable 100 (i.e., it transmits torque to all rotatable parts of the ultrasonic guidewire). Canted coil spring 19 also provides a ground connection to the shielding of inner coaxial cable 100. Thus, canted coil springs 38, 19 effectively provide friction drive.

An area of indentation 202 is provided in mini-connector 24. This indentation 202 provides a means to hold the mini-connector together longitudinally. That is, it prevents axial forces from pulling the various layers of the mini-connector apart longitudinally. Referring now also to FIG. 1*b*, an electrical connection that allows ultrasonic energy to be transmitted from driver 20 to center conductor 103 is provided by spring finger contacts 204. Spring finger contacts 204 are made of metal such as gold-plated beryllium copper.

The thicknesses of the various layers that comprise mini-connector assembly 24 are as follows: spacer layer 190 has a thickness of about 0.001 inch, coil conductor layer 192 has a thickness of about 0.0025 inch, outer insulator layer 194 has a thickness of about 0.001 inch, outer conductor 196 has a thickness of about 0.0025 inch, inner insulator 198 has a thickness of about 0.001 inch, and solid conductor 200 has a thickness of about 0.008 inch.

Manufacture and Assembly of the Ultrasound Imaging Guidewire

A method of connecting the various sections of the ultrasonic guidewire 28 of FIG. 2 is described below. Prior to full assembly, wound flat wire coil layer 110 is formed by winding the individual flat wires around a mandrel, and three sub-assemblies are made. First, drive shaft 1 is connected (e.g., by spot welding) to transducer assembly 23 by connecting (e.g., by spot welding) transducer housing 2 to drive shaft 1. Second, floppy tip assembly 26, which includes core rod 8 and outer floppy layer 7, is formed by known methods, with the proximal end of the core rod free from connection with the surrounding coil at this stage. Third, transition section 34 is formed by inserting elongated trunnion 4 into cylinder 6.

Core rod 8 and outer floppy layer 7 of floppy tip assembly 26 are then mated with the distal end of cylinder 6 by first sliding spacer 138 over core rod 8 and securing it thereto (e.g., by spot welding), and then inserting core rod 8 with the attached spacer 138 into cylinder 6. Note that outer floppy layer 7 slides over cylinder 6 as core rod 8 and spacer 138 slide into cylinder 6. Outer floppy layer 7 and core rod 8, via spacer 138, are then simultaneously secured to cylinder 6 (e.g., by spot welding).

Next, spacer 132 is slid onto the thinner end of elongated trunnion 4 and the combination is inserted into housing 2. The thinner end of elongated trunnion 4 is then simultaneously secured (e.g., by spot welding) to both spacer 132 and housing 2. Coil layer 110 is then slid over the thinner end of cylinder 6 and the ends of the flat wires of coil layer 110 are then attached (e.g., by spot welding) to cylinder 6.

Epoxy 5 may be applied to the areas indicated in FIG. 2, and outer tubular member 29 is then slid over coil layer 110 until it butts up against outer floppy layer 7 of floppy tip assembly 26. Epoxy 5 secures outer tubular member 29 to cylinder 6. A means of attachment, such as epoxy, may also be used between wound flat wire coil layer 110 and outer tubular member 29 to secure coil layer 110 to outer tubular member 29. The epoxy could be applied to either the outside of coil layer 110 or the inside of outer tubular member 29 prior to sliding outer tubular member 29 over coil layer 110.

Outer tubular member 29 may be formed over wound flat wire coil layer 110 by first sliding inner layer 9 over coil layer 110, then sliding outer layer 10 over inner layer 9 and heat-shrinking outer layer 10 to inner layer 9 while the assembly is supported informally by the mandrel. Alternatively, if coil layer 110 is torqued such that its diameter is reduced, outer tubular member 29 may be slid over the reduced-diameter coil layer 110, and when the tension on coil layer 110 is released the coil layer will expand against outer tubular member 29. A means of attachment, such as epoxy, may be used between wound flat wire coil layer 110 and outer tubular member 29 to further secure coil layer 110 to outer tubular member 29, as described previously.

Use

To disconnect ultrasonic guidewire 28 from driver 20, a physician grasps collet assembly 32 and slides it distally away from sterile barrier 30, thus releasing collet assembly 32 and enabling ultrasonic guidewire 28 to be pulled from driver 20 while leaving sterile barrier 30 attached to driver nose 17.

Referring to FIG. 4, ultrasonic guidewire 28 is inserted it into a patient. A clinician introduces the distal end of ultrasonic guidewire 28 through an introducer sheath 116 and into a blood vessel of interest 118, according to standard guidewire techniques. Introducer sheath 116 includes a hemostasis valve 128. Typically, an artery is the vessel of interest. The artery could be a relatively large peripheral vessel, a relatively small proximal coronary artery, or an artery of a size in between. The clinician positions ultrasonic guidewire 28 in the general region of a site of interest 120, such as a stenosis, within the vessel of interest 118 by using, e.g., fluoroscopy.

Figures 5, 5A:
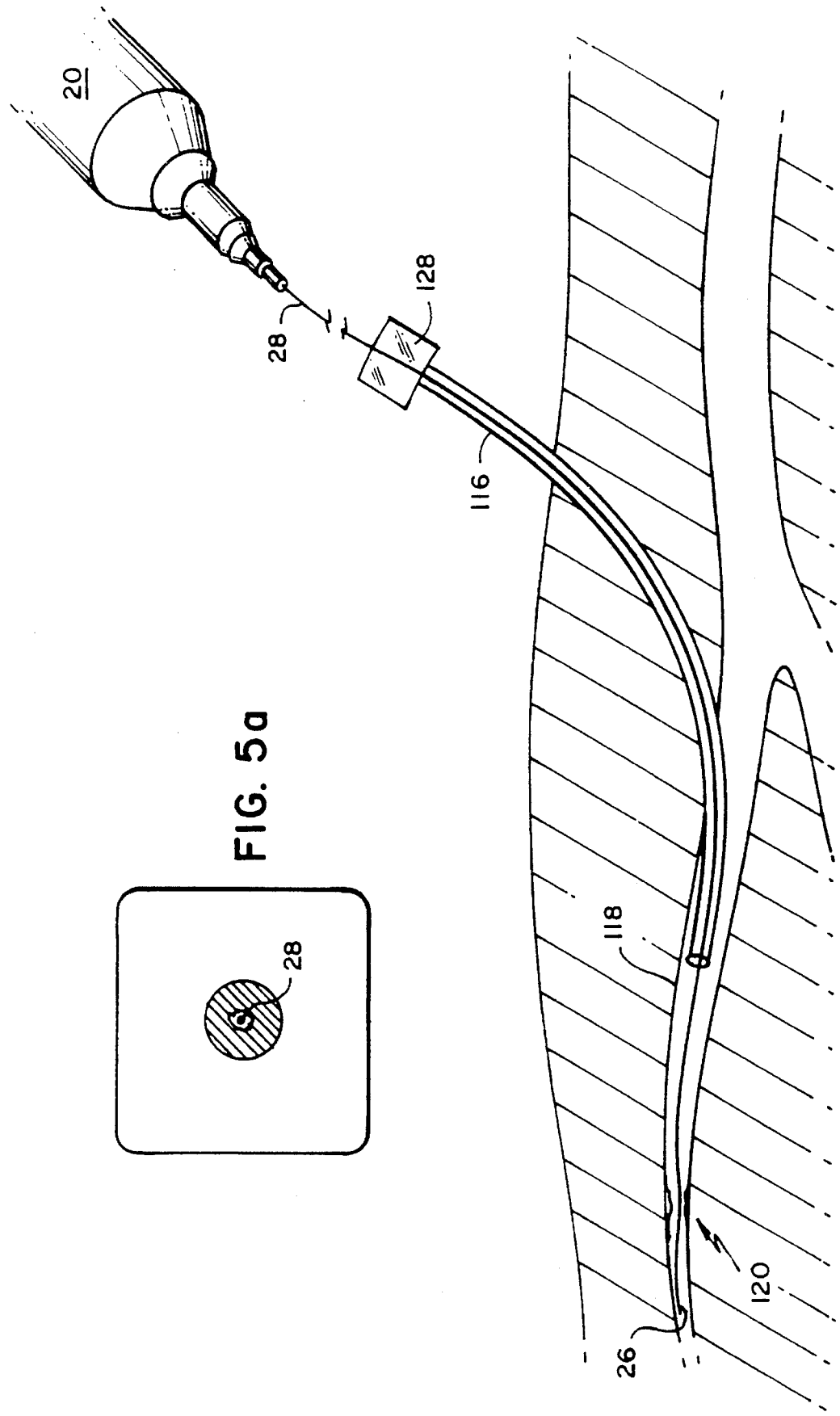

Referring to FIG. 5, after ultrasonic guidewire 28 is placed inside vessel 118, the clinician then connects the proximal end of ultrasonic guidewire 28 to driver 20. With driver 20 attached to ultrasonic guidewire 28, it is possible to obtain real-time, 360° ultrasonic images of vessel 118 with ultrasonic guidewire 28. An example of an ultrasound image associated with FIG. 5 is shown in FIG. 5a. The clinician may both advance and withdraw ultrasonic guidewire 28 during the real-time imaging to more accurately position transducer assembly 23 at the site of interest 120, e.g., a region stenosed with plaque. Thus, use of ultrasonic guidewire 28 allows the clinician to view ultrasonic images while simultaneously moving ultrasonic guidewire 28 within vessel 118.

When ultrasonic guidewire 28 is positioned accurately at the site of interest 120, the clinician disconnects ultrasonic guidewire 28 from driver 20 as shown in FIG. 6 and introduces a therapeutic device such as a standard balloon dilatation catheter 122 over the proximal end of the mini-connector 24 of ultrasonic guidewire 28, using a lumen 160 provided on catheter 122. Balloon catheter 122 is preferably made of a sonolucent material such as polyethylene. Balloon catheter 122 is passed through introducer sheath 116 and into the blood vessel 118. At this point, again, ultrasonic guidewire 28 functions similar to a typical guidewire in that it is not connected to driver 20 and it acts as a guide for balloon catheter 122. Initially, balloon catheter 122 is only partially introduced into the blood vessel 118.

The relatively long length of ultrasonic guidewire 28 allows the proximal end of ultrasonic guidewire 28 to be reconnected to driver 20 without balloon catheter 122 being slid entirely into blood vessel 118. Depending on the distance from the point of entry on the patient's body to the site of interest 120, ultrasonic guidewire 28 may be reconnected to driver 20 without balloon catheter 122 being introduced into the patient's body at all.

As shown in FIG. 6a, with balloon catheter 122 partially introduced into vessel 118 but not at the site of interest 120, the clinician reconnects the proximal end of ultrasonic guidewire 28 to driver 20 by means of collet assembly 32 and sterile barrier 30, as described previously. It is now possible for the clinician to obtain real-time ultrasonic images, and thus precisely position balloon catheter 122 at the site of interest 120. An example of an ultrasound image associated with FIG. 6a is shown in FIG. 6b. Because air is not a sonolucent media, a small amount of inflation fluid (e.g., water or saline mixture) is typically introduced into balloon catheter 122 via a balloon inflation port 130 to make balloon catheter 122 visible to the clinician on the ultrasound image.

With balloon catheter 122 accurately positioned at the site of interest 120 as shown in FIG. 7, the clinician inflates balloon catheter 122 via balloon inflation port 130 to dilate the site of interest 120. The clinician continues to obtain ultrasonic images with ultrasonic guidewire 28 while inflating balloon catheter 122 and watches for any cracks, fissures, or other problems with vessel 118 that may occur during inflation of balloon catheter 122. An example of an ultrasound image associated with FIG. 7 is shown in FIG. 7a.

At the conclusion of the procedure, the clinician deflates balloon catheter 122, removes it from the site of interest 120, and examines the site of interest 120 with ultrasound images obtained by ultrasonic guidewire 28. Depending on the images obtained, the clinician determines whether or not the balloon catheter procedure produced dilatation. If necessary, the clinician can repeat the procedure or remove driver 20 from ultrasonic guidewire 28, remove balloon catheter 122, and insert another (e.g., a larger) balloon catheter, then reconnect ultrasonic guidewire 28 to driver 20, and continue treatment.

Advantageously, the use of ultrasonic guidewire 28 greatly reduces the amount of fluoroscopy needed and therefore the amount of harmful contrast agent required to be introduced into the patient's body.

Other embodiments are within the following claims. For example, the ultrasound imaging guidewire 28 could range in size from about 0.014 to 0.040 inch in maximum outside diameter d (see FIG. 1). Also, solid couplant 11 could be formed from oil-filled polyurethane instead of polystyrene. The entire floppy tip assembly, not just the internal core rod, can be tapered, that is, the outside diameter of the floppy tip assembly can being at an outside diameter substantially equal to the outside diameter of the main guidewire body and taper gradually along its length toward its distal end. The inside of wound flat wire coil layer 110 can, in the region of the transducer, be coated with an anti-echoic material (e.g., an epoxy) to decrease acoustic reflection. Wound flat wire coil layer 110 could comprise more than three flat wires to, among other things, increase stiffness in the window area 31 (see FIG. 3). Referring to FIGS. 8 and 8a, instead of a flat wire, a wire having a convex reflective contour can be used to form coil layer 110 and thereby decrease detrimental acoustic reflection incident on the transducer. The cross-section of the wire preferably has an aspect ratio of about 2-to-1, as indicated in FIG. 8a. FIG. 8b indicates another configuration of the convex wire in cross-section which also has an aspect ratio of about 2-to-1. Other aspect ratios and shapes are also possible. A knitted layer of kevlar could be used in place of wound coil layer 110. It would be preferable to coat inner layer 9 with a thin layer of metal (as described previously) if coil layer 110 is replaced with a knitted layer of kevlar because the kevlar layer would probably not provide adequate RF shielding. The kevlar layer preferably extends over the transducer and is joined in the transition section to transmit torque and tension to the floppy tip assembly.

Referring to FIGS. 2e and 2f, an alternate configuration of the transducer assembly includes a housing 170 having a transducer 164 mounted perpendicular to the length of drive shaft 1, and a mirror 166 disposed at an angle opposite transducer 164 and formed as part of a elongated trunnion 168. As in the embodiment of FIG. 2, elongated trunnion 168 is attached to and rotates with housing 170. Mirror 166 is angled to reflect energy toward an opening (not shown) in housing 170.

Referring to FIG. 2g, in this case the transition section includes an extended rotatable transducer housing 180. A proximal extension of a stationary core rod 182 of a floppy tip assembly extends into rotatable housing 180. A spacer 184 formed of a section of hypotube secured to the extended portion of housing 180 provides a shoulder against which a retainer 186 attached to the proximal end of core rod 8 butts to provide tensile strength and stability (similar to that provided by the combination of elongated trunnion 4 and cylinder 6 shown in FIG. 2). This configuration contributes similar qualities as the transition region previously described. That is, it provides substantially uniform lateral stiffness throughout the respective length of the ultrasonic guidewire.

A method of connecting the various sections of the embodiment shown in FIG. 2g is now described with reference to FIGS. 2h, 2i, 2j, and 2k. Prior to final assembly, a wound flat wire coil layer 210 is formed by winding individual flat wires around a mandrel, and two sub-assemblies are made (FIG. 2h). First, a floppy tip assembly, which includes core rod 182 and an outer floppy layer 212 of wound round wire, is formed by known methods. Second, a drive shaft 214 is connected (e.g., by spot welding) to transducer housing 180.

A hypotube spacer 216 is then secured to housing 180, e.g., by spot welding (FIG. 2h). The floppy tip assembly is then brought up to transducer housing 180 and core rod 182 is inserted into housing 180 through spacer 216 (FIG. 2i). Another hypotube spacer 218 is held in place through the opening in housing 180 while core rod 182 is slid through it and spacer 216 (FIG. 2i). Spacer 218 and core rod 182 are then joined (e.g., by spot welding) via the opening in housing 180. Next, wound flat wire coil layer 210 is slid over housing 182 such that it butts up against outer floppy layer 212 of the floppy tip assembly (FIG. 2j). Coil layer 210 is then attached (e.g., by spot welding) to a floppy tip hypotube spacer 220.

An outer tubular member is then slid over coil layer 210 until it butts up against outer floppy layer 212 of the floppy tip assembly (FIG. 2k). As described previously, either epoxy can be used to secure the outer tubular member to coil layer 210 or by shrink-wrapping the various layers of the outer tubular member. Alternatively, as described previously, coil layer 210 may be torqued such that its diameter is reduced, the outer tubular member may be slid over the reduced-diameter coil layer 210, and when the tension on coil layer 210 is released the coil layer will expand against the outer tubular member. Again, a means of attachment, such as epoxy, may be used between coil layer 210 and the outer tubular member to further secure coil layer 210 to the outer tubular member.

As shown in FIGS. 2j and 2k, it is possible to form a wound coil layer 210 both before and after the area surrounding the transducer assembly. That is, the coiled wires are separated to form a window area, as described previously, but they are recoiled distal to the window area to provide added stiffness and strength in the region just distal to the window area.

Figure 2L:
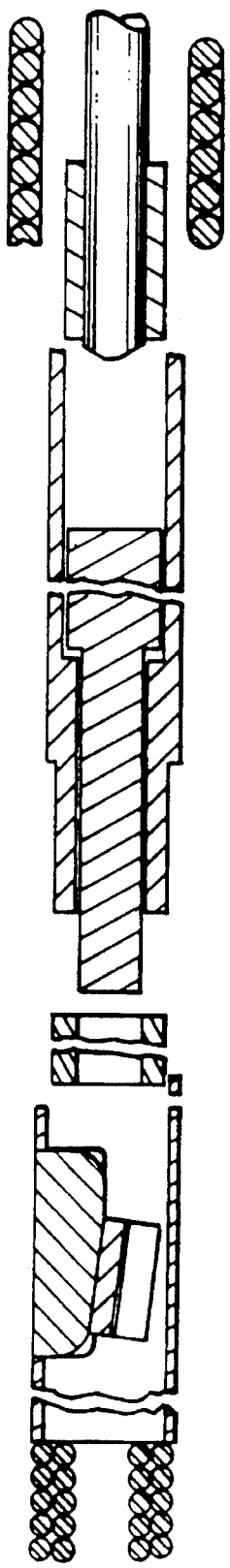

A method of assembly for an ultrasonic guidewire having flat wires that recoil distal to the window area is now described with reference to FIGS. 2l, 2m, 2n, 2o, and 2p. This method is similar to the method for connecting the various sections of the ultrasonic guidewire 28 of FIG. 2 that was described previously under the "Manufacture and Assembly of the Ultrasound Imaging Guidewire" section. As such, prior to full assembly, the wound flat wire coil layer is formed by winding the individual flat wires around a mandrel, and three sub-assemblies are made (FIG. 2l). First, the drive shaft is connected (e.g., by spot welding) to the transducer housing (e.g., by spot welding) of the transducer assembly. Second, the floppy tip assembly, which includes a core rod and an outer floppy layer, is formed by known methods. Third, the transition section is assembled by inserting the elongated trunnion into the cylinder.

Figure 2M:
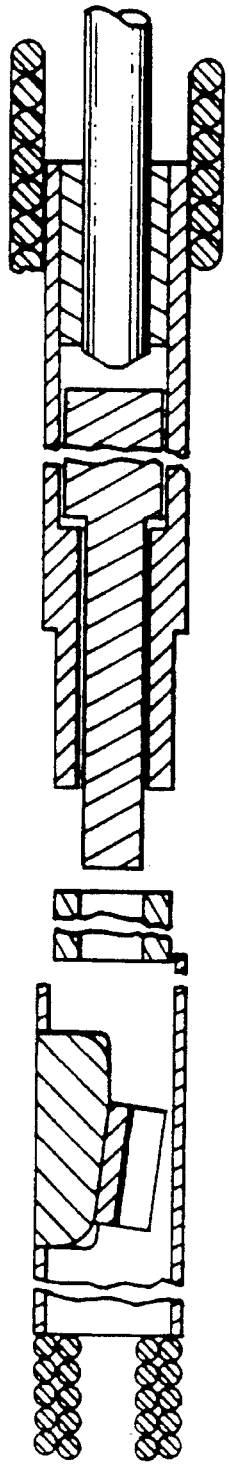

The core rod and the outer floppy layer of the floppy tip assembly are then mated with the distal end of the cylinder by first sliding the core rod spacer over the core rod and securing it thereto (e.g., by spot welding), and then inserting the core rod with the attached spacer into the cylinder (FIG. 2m). Note that the outer floppy layer slides over the cylinder as the core rod and spacer slide into the cylinder. The outer floppy layer and the core rod, via the core rod spacer, are then simultaneously secured to the cylinder (e.g., by spot welding).

Figure 2N:
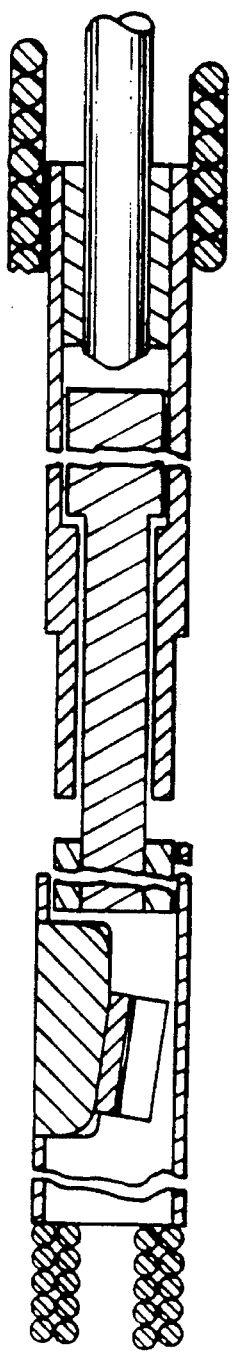

Next, the elongated trunnion spacer is slid onto the thinner end of the elongated trunnion and the combination is inserted into the housing (FIG. 2n). The thinner end of the elongated trunnion is then simultaneously secured (e.g., by spot welding) to both the elongated trunnion spacer and the housing. The coil layer is then slid over the transducer housing and the thinner end of the cylinder (FIG. 2o). The coil layer is then attached (e.g., by spot welding) to the cylinder.

The outer tubular member is then slid over the coil layer until it butts up against the outer floppy layer of the floppy tip assembly (FIG. 2p). A means of attachment, such as epoxy, may be used between the wound flat wire coil layer and the outer tubular member to secure the coil layer to the outer tubular member. The epoxy could be applied to either the outside of the coil layer or the inside of the outer tubular member prior to sliding the outer tubular member over the coil layer.

The outer tubular member may be formed over the wound flat wire coil layer by first sliding the inner polymeric layer over the coil layer, then sliding the outer polymeric layer over the inner layer and shrink-wrapping the outer layer to the inner layer. Alternatively, the coil layer may be torqued such that its diameter is reduced and the outer tubular member may then be slid over the reduced-diameter coil layer. In this case, when the tension on the coil layer is released the coil layer will expand against the outer tubular member. A means of attachment, such as epoxy, may be used between the wound flat wire coil layer and the outer tubular member to further secure the coil layer to the outer tubular member, as described previously.

What is claimed is:

1. A medical guidewire having a substantially uniform small diameter throughout its length and incorporating a lateral acoustic scanning device, said guidewire comprising a proximal connector, an extended main guidewire body portion, an axially elongated transition section, and a floppy tip portion, said main body portion comprising a stationary outer wall including means capable of transmitting torque and, within said outer wall, an elongated rotatable shaft with a distally positioned acoustic scanning device mounted thereon, said proximal connector being constructed to be attached to and detached from a drive device to enable a therapeutic device to be introduced over the guidewire, said connector having a stationary portion secured to said outer wall and an inner drive portion secured to said shaft, said floppy tip portion comprising an outer wire coil and a core rod which tapers from a relatively large diameter, at a proximal joint with said outer wire coil, to a smaller diameter at a floppy distal tip, said transition section joining said main body portion to said floppy tip section in a manner retaining substantially the same lateral stiffness as said main body portion and sufficient torquability to enable torquing of said floppy tip by torque applied to the proximal end of said guidewire.

2. The medical guidewire of claim 1 wherein said connector includes an electrically conductive grounded shaft stub secured to a coil of said rotatable shaft.

3. The medical guidewire of claim 1 wherein said proximal connector is a mini-connector of substantially the same diameter as said main body guidewire portion, a proximal extension of at least the outermost part of the stationary outer wall of said main guidewire body portion extending over and being joined to said mini-connector.

4. The medical guidewire of claim 1 wherein said elongated rotatable shaft has a radial dimension sufficient to provide radial support to said outer wall to prevent kinking thereof.

5. The medical guidewire of claim 1 wherein said rotatable acoustic scanning device is distally supported by an elongated, lateral-load-bearing trunnion, to permit a lateral load to be uniformly transmitted through and from said transition section.

6. The guidewire of claim 1 wherein said transition section which joins said main body portion and said floppy tip portion comprises an axially elongated central member joined to one of said portions, said central member interfitting, with running clearance, with an outer member joined to the other said portion, substantially the full length of said transition section being occupied by structure that imparts lateral stability to render said transition section kink-resistant.

7. The medical guidewire of claim 1 wherein said acoustic scanning device comprises a transducer.

8. A medical guidewire incorporating a lateral acoustic scanning device, said guidewire comprising an extended main guidewire body portion, an axially elongated transition section, and a floppy tip portion, said main body portion comprising a stationary outer wall including means capable of transmitting torque and, within said outer wall, an elongated rotatable shaft with a distally positioned acoustic scanning device mounted thereon, said elongated transition section joining said main body portion to said floppy tip section in a manner retaining substantially the same lateral stiffness as said main body portion and sufficient torquability to enable torquing of said floppy tip by torque applied to the proximal end of said guidewire, said transition section, which joins said main body portion and said floppy tip portion, comprising an axially elongated central member joined to one of said portions, said central member interfitting, with running clearance, with an outer member joined to the other said portion, substantially the full length of said transition section being occupied by structure that imparts lateral stability to render said transition section kink-resistant.

9. The guidewire of claim 8 wherein said central member is an elongated extension which extends from said elongated rotatable shaft distally to an end immediately adjacent to a joint that connects said transition section with an outer wire coil of said floppy tip portion.

10. The guidewire of claim 8 wherein said central member of said transition section comprises a proximal extension of a core rod of said floppy tip portion.

11. The guidewire of claim 10 wherein said acoustic scanning device is disposed in a housing rotatable in conjunction with said rotatable shaft, said housing carrying at its distal end a member having a central bore, said proximal extension of said core rod of said floppy tip extending proximally through said bore and being joined to a retainer element within said housing proximal of said bore.

12. The medical guidewire of claim 8 wherein said stationary outer wall of the main body of said guidewire includes a torsion-transmitting multifilar helical coil, a distal portion of said coil extending over the region occupied by said rotatable acoustic scanning device, the filaments of said coil in said region being substantially spread apart for providing a substantially sonolucent window for said acoustic scanning device, and extremities of said filaments of said coil located distally of said acoustic scanning device being secured to transmit torque to said floppy tip portion.

13. The medical guidewire of claim 8 wherein said acoustic scanning device comprises a transducer.

14. A medical guidewire incorporating a lateral acoustic scanning device, said guidewire comprising an extended main guidewire body portion and a floppy tip portion, said main body portion comprising a stationary outer wall including means capable of transmitting torque and, within said outer wall, an elongated rotatable shaft with a distally positioned acoustic scanning device mounted thereon, said stationary outer wall of the main body of said guidewire including a torsion-transmitting multifilar helical coil, a distal portion of said coil extending over the region occupied by said rotatable acoustic scanning device, the filaments of said coil in said region being substantially spread apart for providing a substantially sonolucent window for said acoustic scanning device, and extremities of said filaments of said coil located distally of said acoustic scanning device being secured to transmit torque to said floppy tip portion.

15. The medical guidewire of claim 14 wherein said filaments have a pitch angle of the order of 45° in the region in register with said acoustic scanning device.

16. The medical guidewire of claim 14 wherein said helical coil is comprised of at least 3 filaments, the width of each filament, in the region in register with said acoustic scanning device, being about ⅓ or less of the corresponding dimension of the aperture of the acoustic scanning device so that a substantial portion of said aperture is unobstructed at any point during rotation of said acoustic scanning device.

17. The medical guidewire of claim 14 wherein the portion of said coil in the region of said acoustic scanning device has an anti-echoic coating.

18. The medical guidewire of claim 14 wherein the portion of said coil in the region of said acoustic scanning device has a convex contour directed inward toward said acoustic scanning device.

19. The medical guidewire of claim 14 wherein the filaments of said torsion-transmitting coil of the wall of said guidewire have a pitch angle that is smaller in a region distal of said acoustic scanning device than in a region in register with said acoustic scanning device, so that turns of said coil in said region distal of said acoustic scanning device, which are closer together than the coil turns in register with said acoustic scanning device, provide the extremities that are joined to said floppy tip portion.

20. The medical guidewire of claim 14 wherein said acoustic scanning device comprises a transducer.

* * * * *

UNITED STATES PATENT AND TRADEMARK OFFICE
CERTIFICATE OF CORRECTION

PATENT NO. : 5,546,948
DATED : August 20, 1996
INVENTOR(S) : Mark A. Hamm, et al.

It is certified that error appears in the above-indentified patent and that said Letters Patent is hereby corrected as shown below:

Column 14, line 30, after "110", the paragraph should not be broken at this point.

Column 15, line 47, replace "21" with --2*l*--.

Column 15, line 54, replace "21" with --2*l*--.

Column 16, line 25, after "coil", the paragraph should not be broken at this point.

Signed and Sealed this

Fifteenth Day of April, 1997

Attest:

BRUCE LEHMAN

Attesting Officer        *Commissioner of Patents and Trademarks*